US 7,585,679 B1

(12) United States Patent
Liu et al.

(10) Patent No.: US 7,585,679 B1
(45) Date of Patent: Sep. 8, 2009

(54) ION CHROMATOGRAPHY SYSTEM WITH FLOW-DELAY ELUENT RECYCLE

(75) Inventors: Yan Liu, Palo Alto, CA (US); Kannan Srinivasan, Tracy, CA (US); Christopher A. Pohl, Union City, CA (US); Sheetal Bhardwaj, Fremont, CA (US); Zhongqing Lu, Fremont, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 12/036,147

(22) Filed: Feb. 22, 2008

(51) Int. Cl.
*G01N 30/02* (2006.01)
(52) U.S. Cl. ...................................... 436/161
(58) Field of Classification Search ................. 436/161
See application file for complete search history.

(56) References Cited

U.S. PATENT DOCUMENTS

| | | | |
|---|---|---|---|
| 5,248,426 A | 9/1993 | Stillian et al. | |
| 5,352,360 A | 10/1994 | Stillian et al. | |
| 6,093,327 A | 7/2000 | Anderson, Jr. et al. | |
| 6,228,333 B1 | 5/2001 | Mueller-Lierheim | |
| 6,610,546 B1 | 8/2003 | Liu et al. | |
| 7,074,331 B2 | 7/2006 | Allington et al. | |
| 7,329,346 B2 | 2/2008 | Liu et al. | |
| 2006/0186046 A1* | 8/2006 | Liu et al. ..................... 210/656 | |

OTHER PUBLICATIONS

Zambelli, T., J.V. Barth, J. Wintterlin, G. Erti, Complex pathways in dissociative adsorption of oxygen on platinum, *Nature*, 390:495-497(1997).
Stipe, B.C., M.A. Rezaei, W. Ho. Atomistic studies of $O_2$ dissociation on Pt(111) induced by photons, electrons, and by heating, *J. Chem. Phys.*, 107(16):6443-6447 (1997).
Verjeij, L.K., M.B. Hugenschmidt. Hydrogen adsorption on oxygen covered Pt(111), *Surface Science*, 324: 185-201 (1995).
Kim, D-H., B-K. Lee, D.S. Lee. Determination of trace anions in concentrated hydrogen peroxide by direct injection ion chromatography with conductivity detection after Pt-catalyzed on-line decomposition, *Bull. Korean Chem. Society*, 20(6):696 (1999).

* cited by examiner

*Primary Examiner*—Walter D Griffin
*Assistant Examiner*—Bobby Ramdhanie
(74) *Attorney, Agent, or Firm*—Morgan, Lewis & Bockius LLP; David J. Brezner

(57) ABSTRACT

A chromatographic method including chromatographically separating sample ionic species in an eluent stream, detecting the separated sample ionic species, catalytically combining hydrogen and oxygen gases or catalytically decomposing hydrogen peroxide in a catalytic gas elimination chamber, and recycling the effluent stream from the chamber to the chromatography separation column. The residence time between the detector and the chamber is at least about one minute. Also, flowing the recycle sequentially through two detector effluent flow channels of an electrolytic membrane suppressor. Also, applying heat or UV energy between the detector and the chamber. Also, detecting bubbles after the chamber. Also, a Platinum group metal catalyst and ion exchange medium in the chamber. Apparatus for performing the methods.

13 Claims, 16 Drawing Sheets

ION CHROMATOGRAPHY SYSTEM WITH FLOW-DELAY ELUENT RECYCLE

BACKGROUND OF THE INVENTION

Since it was introduced in 1975, ion chromatography has become a widely used analytical technique for the determination of anionic and cationic analytes in various sample matrices. In ion chromatography, dilute solutions of acids, bases, or salts are commonly used as the electrolytes in chromatographic eluents.

Traditionally, these eluents are prepared off-line by dilution with reagent-grade chemicals. Off-line preparation of chromatographic eluents can be tedious and prone to operator errors, and often introduces contaminants. For example, dilute NaOH solutions, widely used as the electrolytes in eluents in the ion chromatographic separation of anions, are easily contaminated by carbonate. The preparation of carbonate-free NaOH eluents is difficult because carbonate can be introduced as an impurity from the reagents or by adsorption of carbon dioxide from air. The presence of carbonate in NaOH eluents often compromises the performance of an ion chromatographic method, and can cause an undesirable chromatographic baseline drift during the hydroxide gradient and even irreproducible retention times of target analytes. Therefore, there is a general need for convenient sources, of high purity acid, base, or salt for use as eluents in the ion chromatographic separations.

The continuous operation of an ion chromatography system can consume a significant amount of eluents. The consistent preparation of such large amount of the eluent as well as the disposal of the used eluent can pose serious logistical challenges to the system operators in terms of costs and labor, especially in cases where unattended or less frequently attended operations are required. Even though it overcomes a number of issues associated conventional approaches of eluent preparation in ion chromatography, the use of on-line electrolytic eluent generation devices still requires a constant supply of high purity water from an external source for continuous operation and waste disposal issue remains.

U.S. Pat. No. 7,329,346 describes ion chromatography systems capable of recycling eluents. In one embodiment, the electrolytic suppressor is operated in the recycle mode. The net result of the electrochemical processes in an electrolytic suppressor is that the combined effluent from the suppressor anode and cathode chambers is a mixture of hydrogen gas, oxygen gas, and the aqueous solution containing the eluent components, the ions from the sample injected, and, possibly some trace components derived from the operations of the separation column and suppressor. The effluent from the outlet of the electrolytic suppressor regenerant chamber is passed through the catalytic gas elimination column packed with a Pt catalyst that induces the reaction between hydrogen gas and oxygen gas to form water. The catalytic gas elimination column serves several important functions. First, it provides an elegant means to conveniently eliminate the build up of hydrogen and oxygen gases and thus facilitates the operation of continuous eluent recycle. Second, the water-forming reaction of hydrogen and oxygen is stoichiometric in the column, and the amount of water formed is expected to be in principle the same, as the amount of water consumed originally to produce hydrogen and oxygen gases in the electrolytic operation of the suppressor. In the above embodiment, an analyte trap column is placed after the outlet of a conductivity detector to trap analyte ions. Additionally, ion exchange eluent purification columns packed with appropriate ion exchange resins are used to further purify the regenerated eluent for use for refuse as the ion chromatographic eluent in the separation process.

SUMMARY OF THE INVENTION

In one embodiment of the invention, a chromatographic method is provided including the steps of (a) injecting sample ionic species into an aqueous eluent stream from an eluent source, (b) chromatographically separating the sample ionic species in the eluent stream by flowing the same through chromatographic separation medium to exit as a chromatography effluent, (c) flowing the chromatography effluent through a detector to detect the separated sample ionic species in the chromatography effluent to exit as a detector effluent stream, (d) catalytically combining hydrogen and oxygen gases or catalytically decomposing hydrogen peroxide, or both, in the detector effluent stream by flowing it through a catalytic gas elimination chamber, to form water and reduce the gas content of the eluent effluent stream exiting the gas elimination chamber, and (e) recycling the catalytic gas elimination chamber effluent stream from the catalytic gas elimination chamber to the chromatography separation column, the residence time for flow of the detector effluent stream between the detector and the catalytic gas elimination chamber being at least about one minute to facilitate decomposition of unstable oxidative compounds.

In another embodiment, a chromatographic method is provided comprising the steps of (a) chromatographically separating sample ionic species in an aqueous liquid eluent stream flowing through a chromatography separation medium, to form a chromatography effluent, (b) suppressing the chromatography effluent from step (a) by flowing it through a chromatography effluent flow channel in an electrolytic membrane suppressor to exit as a suppressor effluent stream, (c) flowing the suppressor effluent stream past a flow-through detector to exit as a detector effluent stream, (d) flowing the detector effluent stream from step c) through a first detector effluent flow channel in the membrane suppressor on the opposite side of a first ion exchange membrane from the chromatography effluent flow channel, the detector effluent exiting the first detector effluent flow channel as a recycle stream, (e) flowing the recycle stream through a catalytic gas elimination chamber to catalytically combine hydrogen and oxygen gas, or catalytically decomposing hydrogen peroxide, or both, to form-water thereby reducing the gas content in said recycle stream, and (f) flowing the recycle stream from the catalytic gas elimination chamber to the chromatography separation medium, the time for flow of the detector effluent from the first detector effluent flow channel to the catalytic gas elimination chamber being at least one minute to facilitate decomposition of unstable oxidation compounds.

In another embodiment, a chromatographic method is provided comprising the steps of (a) injecting sample ionic species into an aqueous eluent stream from an eluent source, (b) chromatographically separating sample ionic species in an aqueous liquid eluent stream flowing through a chromatography separation medium, to form a chromatography effluent, (c) suppressing the chromatography effluent from step (a) by flowing it through a chromatography effluent flow channel in an electrolytic membrane suppressor to exit as a suppressor effluent stream, (d) flowing the suppressor effluent stream past a flow-through detector to exit as a detector effluent stream, (e) flowing the detector effluent stream from step (c) through a first detector effluent flow channel in the membrane suppressor on the opposite side of a first ion exchange membrane from the chromatography effluent flow channel, and then through a second detector effluent flow channel on the opposite side of a second ion exchange membrane in the membrane suppressor from the chromatographic effluent flow channel, the detector effluent exiting the second detector effluent flow channel as a recycle stream, (f) flowing the recycle stream through a catalytic gas elimination chamber to catalytically combine hydrogen and oxygen gas, or catalytically decomposing hydrogen peroxide, or both, to form water thereby reducing the gas content in said recycle stream, and (g) flowing the recycle stream from the catalytic gas elimination chamber to the chromatography separation medium.

In another embodiment, a chromatographic method is provided comprising the steps of (a) injecting sample ionic species into an aqueous eluent stream, (b) chromatographically separating the sample ionic species in the eluent stream by flowing the same through chromatographic separation medium, (c) detecting the separated sample ionic species in the eluent stream effluent from said chromatographic medium, (d) catalytically combining hydrogen and oxygen gases or catalytically decomposing hydrogen peroxide, or both, in the eluent stream in a catalytic gas elimination chamber, to form water and reduce the gas content in an eluent stream, in an effluent stream flowing from said catalytic gas elimination chamber, and (e) detecting bubbles in the catalytic gas elimination chamber effluent stream.

In another embodiment, a chromatographic method is provided comprising the steps of (a) injecting sample ionic species into an aqueous eluent stream, (b) chromatographically separating the sample ionic species in the eluent stream by flowing the same through chromatographic separation medium, (c) detecting the separated sample ionic species in the eluent stream effluent from the chromatographic medium, (d) catalytically combining hydrogen and oxygen gases or catalytically decomposing hydrogen peroxide, or both, in the eluent stream in a catalytic gas elimination chamber, to form water and reduce the gas content in an eluent stream, effluent exiting from the catalytic gas elimination chamber; and (e) between steps (c) and (d), applying energy to the gas elimination effluent to decompose at least a portion of any unstable oxidative compound therein.

In another embodiment, a chromatograph apparatus is provided including (a) a chromatography column defining a column lumen, (b) flow-through chromatographic separation medium disposed in the column lumen, the separation medium defining liquid flow-through passages, (c) a detector, (d) a conduit for an aqueous liquid eluent stream providing fluid communication between the detector and the chromatographic separation medium, (e) a catalytic gas elimination chamber in fluid communication with the conduit and including a catalyst for combining hydrogen and oxygen gases, or for catalytically decomposing hydrogen peroxide, or both, in the eluent stream to form water and reduce the gas content in the eluent stream, and (f) a delay conduit disposed between the detector and the catalytic gas elimination chamber, the delay conduit having a total flow-through volume of at least 0.5 times the total volume of said separation medium flow-through passages.

In another embodiment, a chromatography apparatus is provided including (a) chromatographic separation medium, (b) a detector, (c) a membrane suppressor comprising a chromatography effluent flow channel, first and second detector effluent flow channels, and first and second ion exchange membranes separating the chromatography effluent flow channel from the first and second detector effluent flow channels, respectively, (d) a first conduit providing fluid communication between the separator medium and the chromatography effluent flow channel, (e) a second conduit providing fluid communication between the membrane suppressor chromatography effluent flow channel and the detector, (f) a third conduit providing fluid communication between the detector and the first detector effluent flow channel, (g) a fourth conduit providing fluid communication between the first and second detector effluent flow channels, (h) a fifth conduit providing fluid communication between the second detector effluent flow channel and the separation medium, and (i) a catalytic gas elimination device in fluid communication with at least one of the first, second or third conduits and including a catalyst for combining hydrogen and oxygen gases in at least one of the conduits.

In another embodiment, a chromatography apparatus is provided including (a) chromatographic separation medium, (b) a detector, (c) a conduit for an aqueous liquid eluent stream providing fluid communication between said detector and said chromatographic separation medium, (d) a catalytic gas elimination chamber in fluid communication with the conduit and including a catalyst for combining hydrogen and oxygen gases, or for catalytically decomposing hydrogen peroxide, or both, in the eluent stream to form water and reduce the gas content in said eluent stream, and (e) a bubble detector downstream of the catalytic gas elimination chamber and in fluid communication therewith.

In another embodiment, a chromatography apparatus including (a) chromatographic separation medium, (b) a detector, (c) a conduit for an aqueous liquid eluent stream providing fluid communication between the detector and the chromatographic separation medium, (d) a catalytic gas elimination chamber in fluid communication with the conduit and including a catalyst for combining hydrogen and oxygen gases, or for catalytically decomposing hydrogen peroxide, or both, in the eluent stream to form water and reduce the gas content in the eluent stream, and (e) an energy generator disposed between and in fluid communication with the detector and the catalytic gas elimination chamber.

In another embodiment, a catalytic gas and ionic species removal device is provided including a liquid flow-through housing, a platinum group metal catalyst for catalytically combining hydrogen and oxygen gases or for catalytically decomposing hydrogen peroxide, or both, disposed in the housing, and flow-through ion exchange medium disposed in the housing.

In another embodiment, a method is provided of catalytically combining hydrogen and oxygen gases, or for catalytically decomposing hydrogen peroxide, or both, and of removing analyte ions, counter-ions, or both, in a flowing liquid sample stream, the method comprising combining hydrogen and oxygen gases or catalytically decomposing hydrogen peroxide in a liquid sample stream containing ions by flowing the liquid sample stream through a flow-through catalytic device containing a platinum group metal catalyst capable of catalyzing the combining or decomposing, and removing the ions from the liquid sample stream in the flow-through device by contact with flow-through ion exchange medium disposed in the device.

In another embodiment, a chromatographic method is provided including the steps of (a) injecting sample ionic species into an aqueous stream, (b) chromatographically separating the sample ionic species in the aqueous stream by flowing the same through chromatographic separation medium while applying an electric field across the separation medium, to exit as a chromatography effluent, (c) flowing the chromatography effluent through a detector to detect the separated sample ionic species in the chromatography effluent to exit as a detector effluent stream, (d) catalytically combining hydrogen and oxygen gases or catalytically decomposing hydrogen peroxide, or both, in the detector effluent stream by flowing it through a catalytic gas elimination chamber, to form water and reduce the gas content of the eluent effluent stream exiting the gas elimination chamber, and (e) recycling the catalytic gas elimination chamber effluent stream from the catalytic gas elimination chamber to the chromatography separation column.

In another embodiment, a chromatography apparatus is provided including (a) a chromatography column including chromatographic separation medium disposed in the column lumen, (b) spaced electrodes in electrical communication with the separation medium and disposed to pass an electric current through the separation medium, (c) a detector, (d) a conduit for an aqueous liquid stream providing fluid communication between the detector and the chromatographic separation medium, and (e) a catalytic gas elimination chamber in fluid communication with the conduit and including a catalyst for combining hydrogen and oxygen gases, or for catalytically-decomposing hydrogen peroxide, or both, in the eluent stream to form water and reduce the gas content in the eluent stream.

DETAILED DESCRIPTION OF THE INVENTION

The system of the present invention is useful for determining ionic species which are solely anions or cations. Suitable liquid samples include surface waters, other liquids such as industrial chemical waste, body fluids, beverages or drinking water. The term "ionic species" includes molecular species in ionic form and molecules which are ionizable under the conditions of the present invention. The term "eluent" refers to the solution flowing in a liquid chromatography system which carries a sample to be detected. At times herein, the term eluent also refers to the electrolyte in that solution. The eluent normally is water-based but can include an organic solvent so long as it is electrochemically stable.

In certain embodiments, the invention includes a suppressor. The purpose of a suppressor is to reduce the conductivity and noise of the analysis stream background while enhancing the conductivity of the analytes (i.e., increasing the signals/noise ratio), while maintaining chromatographic efficiency.

In other embodiments, the invention relates to improved catalytic gas removal devices and methods and to improved systems for using catalytic gas removal devices and systems disclosed in U.S. Pat. No. 7,329,346, incorporated in its entirety by reference. The invention will first be described for the embodiment of FIG. 1.

Figure 1:
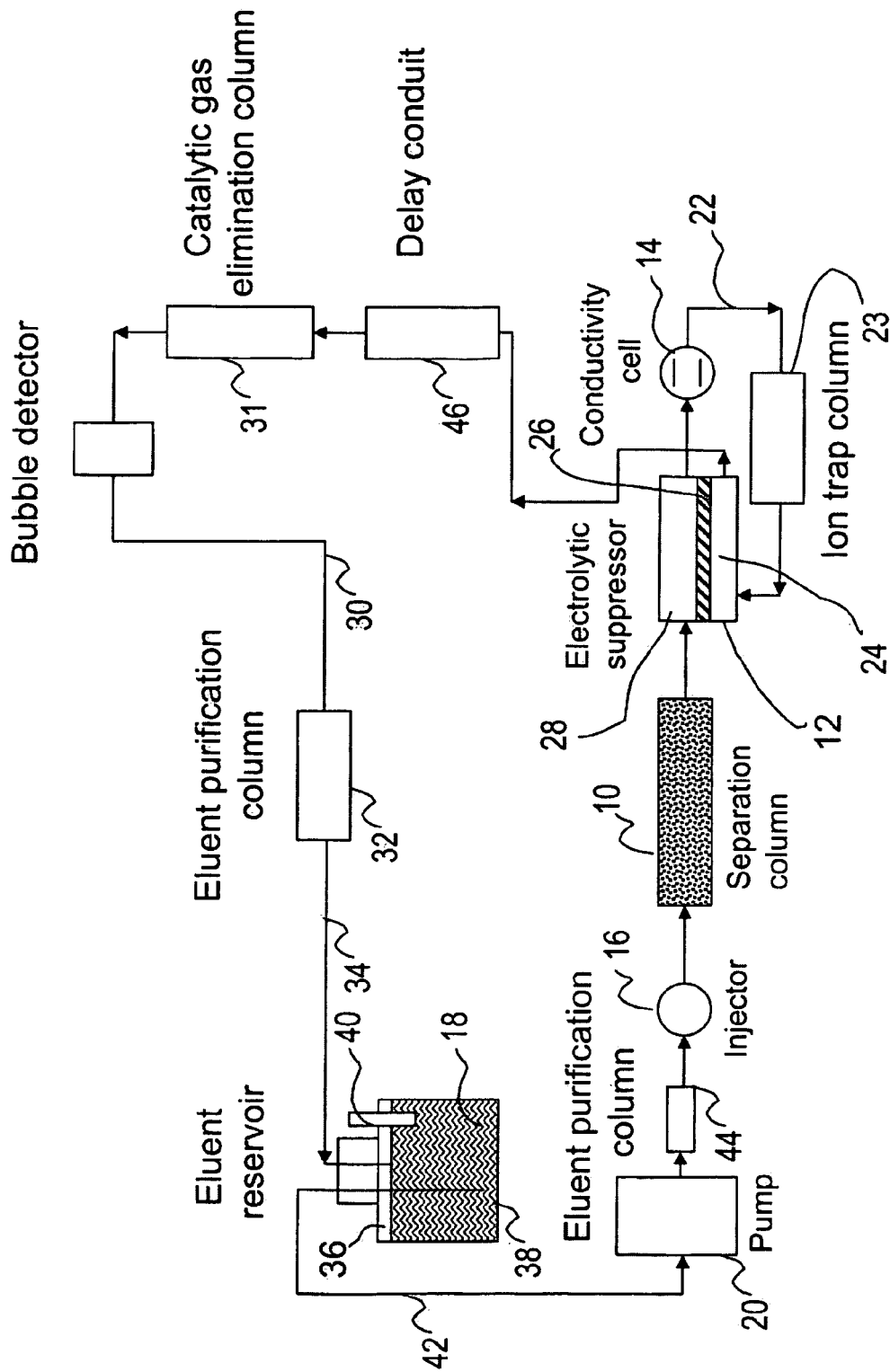
FIGS. 1-8 are schematic representations of apparatus according to different embodiments of the present invention.

Referring to FIG. 1, a simplified apparatus for performing the present invention is illustrated. This system includes a suppressor with recycle of the effluent from a detector to the suppressor. That portion of the system is similar to the general system illustrated in U.S. Pat. No. 5,248,426. In the present invention, the effluent from the suppressor is recycled to the separation column, preferably after mixed with an eluent in an effluent reservoir, as part of the eluent electrolyte used for separation. In a preferred embodiment, one or more eluent purification columns such as ion trap columns are used in the system to remove contaminants, typically in ionic form, in the recycled stream prior to use as an eluent in the separation column.

Referring again to FIG. 1, the system includes chromatographic separation medium, typically in the form of chromatographic separation medium chromatographic column 10. (As used herein, the term "column" refers to a flow-through housing with an interior chamber in any configuration for performing the indicated function). Any known chromatographic separation medium may be employed including ion exchange resin in a resin bed, monolith, or other form, a porous hydrophobic chromatographic resin permanently attached to ion exchange sites, and medium used for mobile phase ion chromatography (MPIC).

Arranged in series with column 10 is a suppressor 12 serving to suppress the conductivity of the electrolyte of the eluent from column 10 but not the conductivity of the separated ions. The effluent from suppressor 12 is directed to a detector, preferably in the form of a flow-through conductivity detector cell 14, for detecting the ion species resolved in column 10. A suitable sample including ionic species is supplied through sample injection valve or injector 16 which is passed through the apparatus in the solution of eluent from an eluent source or reservoir 18 drawn by pump 20 which then passes through injection valve 16. The chromatography effluent solution leaving column 10 is directed through suppressor 12 wherein the electrolyte is converted to a weakly conducting form. The chromatography effluent from suppressor 12 passes through detector 14, schematically illustrated as a conductivity cell, in which the presence of ionic species produces an electrical signal proportional to the amount of ionic material. Such a signal is typically directed from detector 14 to a conductivity meter (not shown). Any other known detector useful for detecting ionic species in a chromatography system nay also be employed including absorbance and electrochemical detectors.

In one embodiment, the effluent from conductivity detector 14, referred to as the detector effluent, is directed in a recycle conduit 22 to at least one flow-through detector effluent flow channel 24 in suppressor 12. An ion exchange membrane 26 separates detector effluent flow channel 24 from chromatographic separation effluent flow channel 28 which receives the effluent from chromatography column 10. In the simplified version illustrated, only a single detector effluent flow channel 24 is used. The system of the present invention is also applicable to other membrane suppressors such as the sandwich suppressor type illustrated in U.S. Pat. No. 5,248,426. In a sandwich suppressor, the chromatographic separation effluent flows through a central flow channel flanked by two detector effluent flow channels separated by ion exchange membranes. In this embodiment, the detector effluent flow channels may be supplied with the detector effluent from conductivity detector 14 by use of a splitter valve. The details of such a sandwich suppressor and the use of recycle from the conductivity cell are supplied by the detector effluent flow channel as illustrated in U.S. Pat. No. 5,248,426. As illustrated, for anion analysis, the detector effluent flow channel is positively charged and hydronium ions are generated for passage through membrane 26 according to the following equation:

For anion analysis, in the chromatography effluent flow channel, cations of the electrolyte, e.g., sodium ions, pass through membrane 26 into the detector effluent flow channel 12 toward a cathode, not shown, for electrolytic suppressor. Hydroxide is converted to water according to the following equation:

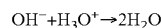

Figure 3:
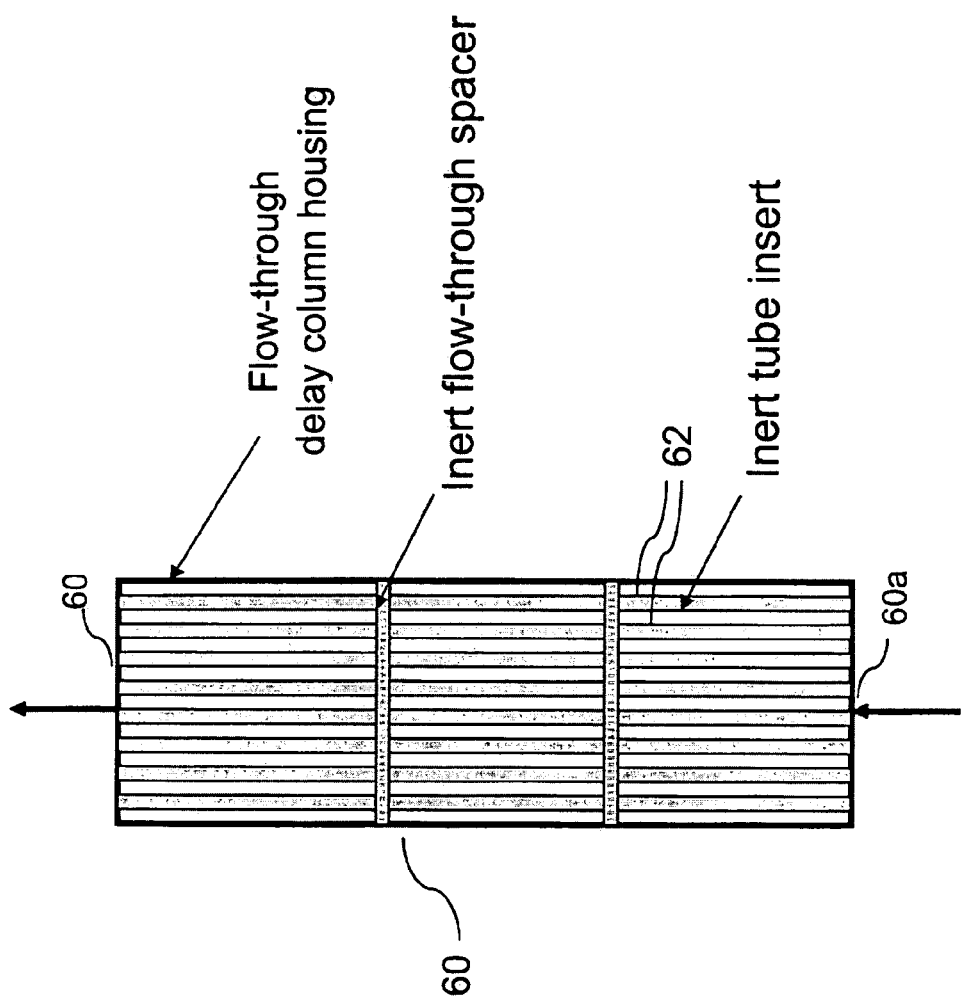
Figure 4:
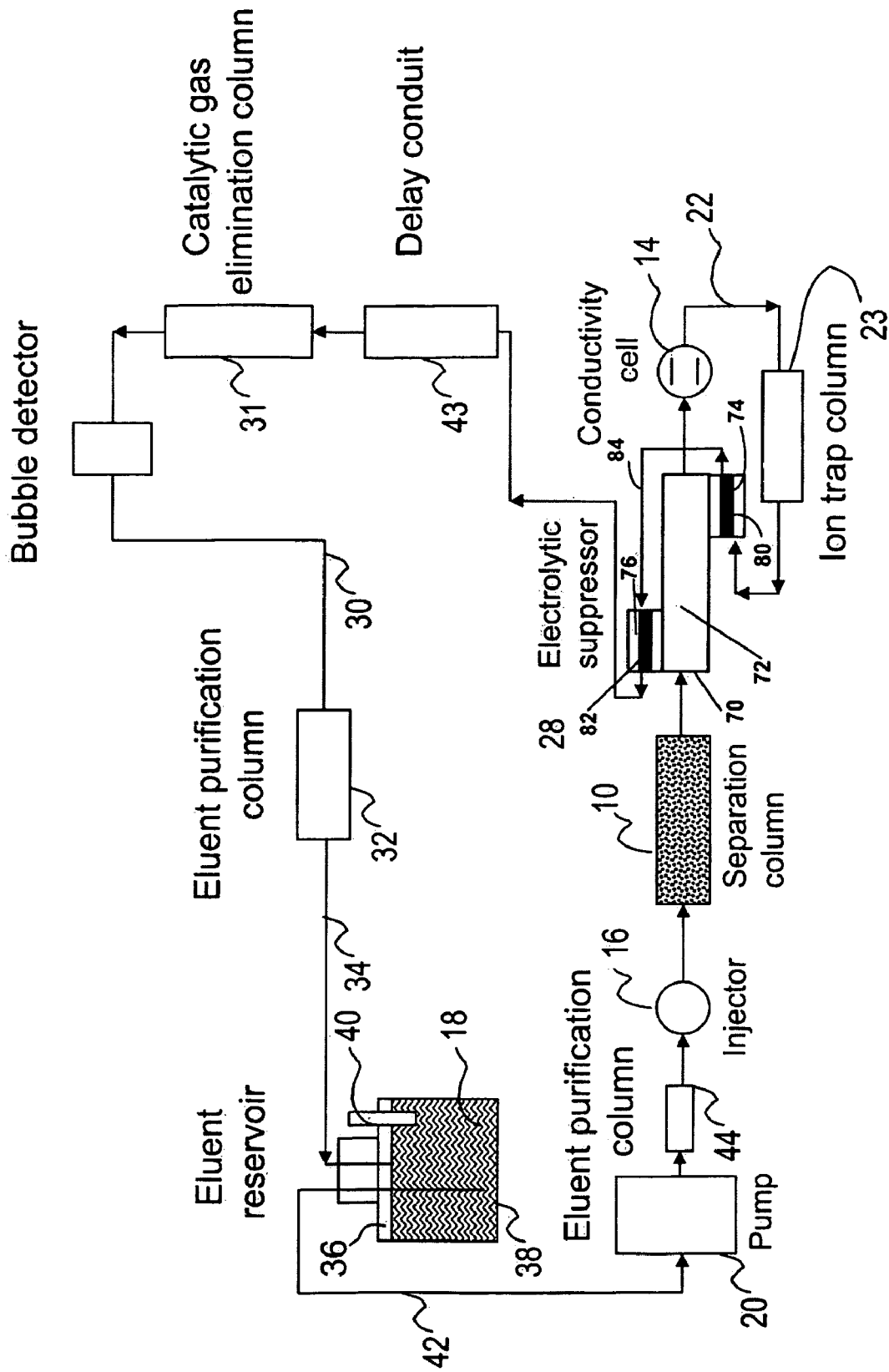

In one preferred embodiment, the suppressor is of the electrolytic type as illustrated in FIGS. 3 and 4 of U.S. Pat. No. 5,352,360.

Suitable eluent solutions for anion ion chromatography include alkali hydroxides, such as sodium hydroxide, alkali carbonates and bicarbonates, such as sodium carbonate, alkali borates, such as sodium borate, combinations of the above, and the eluent systems of the aforementioned patents.

The recycle system of the present invention is also applicable to the analysis of cations (e.g., lithium, sodium, ammonium, potassium, magnesium, and calcium). In this instance, the electrolyte of the eluent is typically an acid which does not damage the membrane. Methanesulfonic acid has been found to be inert to the membrane under electrolytic conditions. Other acids such as nitric acid and hydrochloric acid produce electrochemical by-products that may damage the membrane and are, thus, not generally preferred for that typical membrane.

In the effluent recycle system of U.S. Pat. No. 5,248,426, the effluent from the detector effluent flow channel is directed to waste. In contrast, in the system of FIG. 1, the effluent stream is redirected to the separation, column 10, preferably by flowing through the eluent reservoir 18. The FIG. 1 embodiment is similar to the system of U.S. Pat. No. 7,329, 346 incorporated by reference, except for the flow delay prior to the catalytic gas elimination column.

Referring specifically to FIG. 1, the effluent from the detector effluent channel flows in line 30 through catalytic gas elimination column 31, optional delay conduit 46, and optional eluent purification column 32 and from there through tubing projecting, through a closure 36 of container 38 of eluent reservoir 18. An optional gas vent 40 is provided in reservoir container 38 to vent hydrogen and oxygen gases which are generated electrolytically in the system. Eluent solution from reservoir 18 is directed in line 42 to separation column 10 as the source of eluent for separation. As illustrated, the eluent in line 42 flows through pump 10 and optional eluent purification column 44 prior to separation column 10.

Also as illustrated in FIG. 1, optional ion trap column 23 can be placed in line 22 between conductivity cell 14 and suppressor 12. Preferably, the ion trap column 23 is packed with anion exchange resin in carbonate form for anion analysis using carbonate eluents or anion ion exchange resin in the hydroxide form for anion analysis using hydroxide eluents. Typically, it only removes ions of one charge, positive or negative. For cation analysis using acid eluents, the ion trap column may be packed with cation exchange resin in the hydronium form. The ion trap column serves the function for retaining analyte ions in the suppressed eluent.

For a system in which eluent is recycled from the detector to the separation column, it is preferable to remove contaminants of sample injected through injection valve 16, and other trace contaminants may be generated from operation of the ion chromatography system. This can be performed by using one or both of purification columns 32 or 44. One form of eluent purification column preferably includes an inlet section and an outlet section, not shown, with a strongly acidic cation exchange material, e.g., resin in the inlet section, preferably in the form of the cation of the eluent used. For example, the resin preferably in the form of sodium for a sodium carbonate eluent or in the hydronium form for a sulfuric acid eluent. The outlet section may be packed with strongly basic cation exchange material, e.g., resin in the form of the anion of the flowing eluent. For example, the form may be carbonate for the sodium carbonate eluent or sulfate for the sulfuric acid eluent. It is preferable to use highly cross-linked and macroporous high area for both the cation exchange resin and the anion exchange resin used in purification columns. It is preferable to use resins having cross-linking of at least 20%, preferably at least 30% and surface area of at least 10 $m^2/g$ preferably at least 20 $m^2/g$. Such resins are effective in removing components of they injected sample and other trace contaminants generated in the system. Examples of such resins include. AG MP-50 strongly acidic cation exchange resin and AG MP-1M strongly basic anion exchange resin available from Bio-Rad (Hercules, Calif.). Other forms of optional eluent purifiers may be employed.

Optionally, the eluent purification columns 32 or 44 may also include an additional section of neutralized porous resin, preferably of high surface area to remove non-charged contaminants in the recycle eluent. In the illustrated embodiment, a larger eluent purification column 32 is placed upstream of suppressor 12 in comparison to the optional smaller purification column 44 placed at the outlet of pump 20 to further purify the eluent prior to entering separation column 10. Suitably, column 32 has an ion exchange capacity of at least 0.5 milliequivalents.

In general, the eluent purification column and the ion trap column remove the ions from the sample injected and some trace components derived at the system. When the purified eluent is recycled back into eluent reservoir 18, the solution typically contains a mixture of electrolytically generated hydrogen gas and oxygen gas. Some of these gases may be removed from the eluent reservoir 18 equipped through a gas vent port 40.

A catalytic gas elimination column 31 is particularly useful in a system in which an electrolytic suppressor with detector, effluent recycle to the suppressor regeneration flow channel, e.g. of the type disclosed in U.S. Pat. No. 5,248,426, is used. Such a system, sold by Dionex Corporation under the trademark SRS, can be used for anion analysis, e.g., using a sodium carbonate eluent. In this mode, the effluent from the detector cell is used as the source of water for the electrolysis reactions in the anode and cathode chambers of the suppressor. Under the applied electrical field, water is oxidized to form hydronium ions and oxygen gas at the anode and reduced to hydroxide ions and hydrogen gas at the cathode. The hydronium ions migrate across the cation exchange membrane into the eluent chamber of the suppressor to react with carbonate ions in the eluent to form carbonic acid which is only weakly conductive. In the meantime, the counter ion in the sample injected (e.g., $Na^+$) is replaced with hydronium ion and forced to migrate across another cation exchange membrane into the cathode chamber of the device. The analyte anion, $X^-$, is detected in the more conductive form of $H^+ + X^-$ by the conductivity detector. The net result of the electrochemical processes is that the combined effluent from the suppressor anode and cathode chambers is a mixture of hydrogen gas, oxygen gas, and the aqueous solution containing the ionic eluent components, the ions from the sample injected, and possibly some trace components derived from the operations of the separation column and suppressor.

The electrolysis reactions in the anode and cathode chambers of the electrolytic suppressor may lead to the formation of reactive or oxidative species. For example, ozone may be formed in the anode chamber of the electrolytic suppress or ($H_2O \rightarrow 2H^+ + 2e^- + \frac{1}{3}O_3$). Hydrogen peroxide may be formed in the cathode chamber of the electrolytic suppressor ($2H_2O + O_2 + 2e^- \rightarrow 2OH^- + H_2O_2$). When an anion electrolytic suppressor is used to suppress sodium carbonate eluents, the electrolytic formation of sodium percarbonate may also occur in the anode chamber. The presence of these unstable reactive or oxidative species in the effluent of an electrolytic suppressor may have detrimental effects on the performance of ion chromatography system with eluent recycle.

The unstable reactive or oxidative species such as ozone, hydrogen peroxide, and sodium percarbonate may attack the ion exchange functional groups in the eluent purification column and the separation column in the system and degrade the ion exchange capacity of the columns. If the eluent purification column and the separation column lose their desired ion exchange capacity, the performance of an ion chromatography system with eluent recycle is compromised. For example, the gradual loss of the ion exchange capacity of the separation column leads to the downward drift of retention time of target analytes separated on the separation column. The gradual loss of the ion exchange capacity of eluent purification columns reduces their capability in removing components of samples injected and other trace contaminants that may be generated from the operation of the entire ion chromatography with eluent recycle.

Thus, the aqueous recycle stream which flows through catalytic gas elimination column 31 can include unstable oxidative compounds such as ozone and sodium percarbonate. Such unstable oxidative compounds typically have a relatively short half-life time. For example, ozone had a half-life time of about 3 minutes at pH 9.2 and decomposes into oxygen in aqueous solution. Therefore, it is advantageous to provide a time delay in the system, particularly between the electrolytic suppressor and the catalytic gas elimination column. This would permit the unstable oxidative species that may present in the electrolytic suppressor regenerant channel 12 effluent recycled to catalytic gas elimination column 31 to decompose into non-reactive or non-oxidative species. Another advantage of the time delay would be to minimize their potential detrimental effects on the ion exchange functional groups in eluent purification column 32 and separation column.

Absent a time delay, such as performed in delay conduit 46, flow of the recycle stream through a system of the type illustrated in FIG. 1 between either cell 14 or suppressor 12 and catalytic gas elimination column 31 would take a relatively short time. According to one embodiment of the invention, to facilitate decomposition of unstable oxidative compounds, the residence time for flow between the detector and the catalytic gas elimination column is at least 1 minute, preferably at least 2 minutes, more preferably at least 5 to 20 minutes or more. According to another embodiment, the time for flow of recycle from detector effluent flow channel 24 of suppressor 12 and catalytic gas elimination column 31 is at least 0.5. minutes, preferably at least 2 minutes, more preferably at least 5 to 20 minutes or more.

As used herein, the term "residence time" encompasses the time for online flow between the designated devices and also the delay time for stopped flow in a discontinuous system. For example, with appropriate valving, part of the recycle stream could be sent to a stopped flow chamber and the flow toggled between the stopped flow and online continuous flow. Thus, the residence time would include the time that the recycle solution is in a stopped flow chamber. Preferably, in this system, all flow from the detector is sent to the stopped flow chamber for the desired time.

As used herein, the term "delay conduit" refers to all tubing and devices through which the recycle stream flows between the detector or the suppressor and the catalytic gas elimination column, depending on the context of use of this term regarding the end points of the delay conduit.

Figure 2:
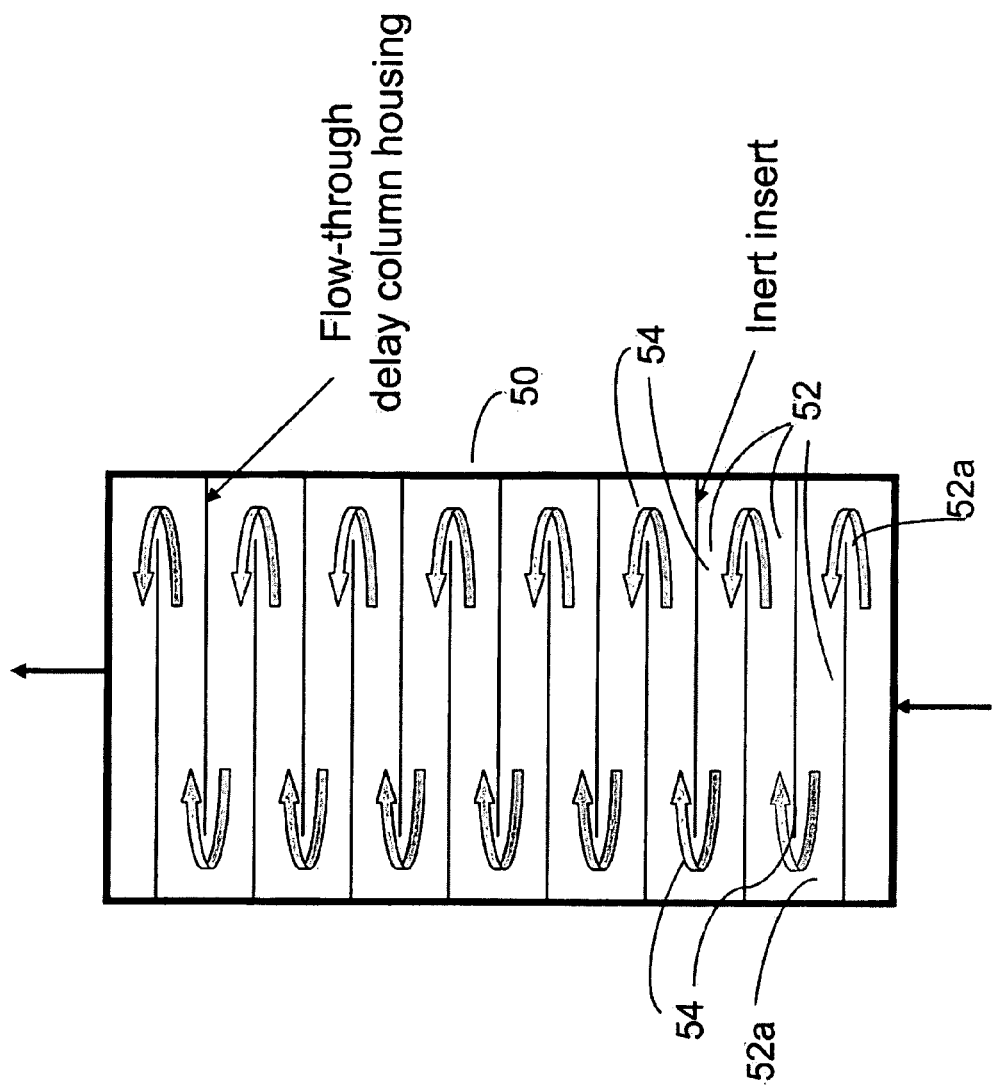

In one embodiment, the delay conduit includes a delay housing and the detector effluent stream flows from the detector (or the suppressor) in a tortuous path, such as a serpentine path, to maximize the residence time of gas bubbles in the device. One such delay conduit is illustrated in FIG. 2. It includes flow-through housing or column 50, e.g. of cylindrical shape, with inlet and outlet ports 50a and 50b, respectively. As illustrated, disposed in housing 50 are baffles 52 with flow openings 52a, unaligned in the direction of flow to cause the recycle solution to flow in a non-linear path 54 and thus delay flow.

FIG. 3 shows another embodiment of a flow-through delay column. In this embodiment, the delay column is packed with segments of multiple thin-wall tubes so that there are multiple pathways for the gas bubbles to move through the delay column to increase their effective residence time in the delay column. Referring specifically to FIG. 3, column 60 includes inlet and outlet 60a and 60b, respectively. It includes a plurality of tubes 62, each being in parallel communication with the detector. The detector effluent flowing into column 60 through inlet 60a is split into multiple streams through tubes 62 and recombined on exit through outlet 60b, thereby delaying the time of flow and increasing the residence time of the recycle stream and gas bubbles in the column.

In another embodiment, not shown, the delay-conduit can includes a large volume device which is open or filled with packing other than the baffles of FIG. 2 to further delay flow. Such packing can include a packed bed, e.g. of polypropylene beads or a porous, polymer monolith.

In another embodiment, not show the delay conduit may comprise long tubing. For space considerations, such long tubing would preferably be coiled, e.g. in a spool of inert polymeric tubing of appropriate internal diameter and length. The tubing may be fitted with appropriate inlet and outlet fittings. It is preferred that such tubing would have an appropriate wall thickness and is substantially impermeable to hydrogen and oxygen gases so that there is no leakage of hydrogen or oxygen gas across the wall of the tubing. If the leakage of hydrogen and oxygen gas occurs, the stoichiometric ratio of hydrogen and oxygen gases entering the catalytic gas elimination column would be altered and thus the water-forming reaction of hydrogen and oxygen becomes non-stoichiometric in the catalytic gas elimination column, leading to incomplete removal of hydrogen and oxygen gas. In an ion chromatography system with eluent recycle, the incomplete removal of hydrogen and oxygen gas by the catalytic gas elimination column may result in the accumulation of hydrogen gas in the eluent reservoir and thus a potential explosion risk. Therefore, it is preferred that there is no leakage of hydrogen or oxygen gas across the wall of the flow-through delay tubing.

Another embodiment of the flow-through delay conduit takes a form of a chamber as in a chromatographic column housing with flow-through end fittings. The column housing should have appropriate internal diameter and length to provide the desirable delay volume. The effluent from an electrolytic suppressor is a mixture of $H_2$, $O_2$, and $O_3$ gases, and the aqueous solution containing mainly the ionic eluent components. Because the effluent from an electrolytic suppressor is a gas-liquid mixture, it is desirable to maximize the residence time of ozone-containing gas bubbles in such a flow-through delay column. If the delay column is mounted vertically, the ozone-containing gas bubbles may effervesce rapidly in an upward direction through the internal chamber of the flow-through delay column so that the effective residence time in the delay column is reduced. Therefore, it may be preferred to mount the delay column horizontally so that gas bubbles move at the same rate that the liquid flows through the column.

The chromatographic column defines a column lumen in which flow-through chromatographic medium is disposed. The medium, e.g. a packed bed or a monolith, defines liquid flow-through passages. The total volume of such passages can be measured by the volume of liquid retained by the column with the medium in place. This will be referred to as the total volume of the flow-through passages or "the chromatography column void volume." Similarly, the delay conduit may include various types of packing. The total volume of the delay conduit is defined by the total volume of liquid which would be retained by the full length of the various components of the delay conduit in stopped flow.

In one embodiment, the delay conduit flow-through total volume preferably is at least 0.5 times, more preferably at least 1 or 2 times, most preferably at least 3, 4, 5 times or more, the total volume of the flow through passages of the chromatography column.

In another embodiment also applicable to the chromatographic column embodiment, the delay conduit includes a delay housing having a cross-sectional area transverse to fluid flow at least 3, 4, 5 times, more preferably at least 8, 9, 10 times, and most preferably at least 15 or 20 times or more, the cross-sectional area of tubing in the recycle conduit.

The embodiment of FIG. 4 is similar to that of FIG. 1, and so like parts with FIG. 1 will be designated with like numbers. Here, electrolytic suppressor 70 includes a chromatography effluent flow channel 72, filled with ion exchange packing and first and second detector effluent flow channels 74 and 76, respectively, in electrical communication with electrodes 80 and 82, respectively. Ion exchange membranes, not shown, separate the first and second detector effluent flow channels 74 and 76 from chromatography effluent flow channel 72. A conduit 84 connects the outlet of flow channel 74 with the inlet of flow channel 76.

In this embodiment, the detector effluent flows sequentially through the anode chamber and cathode chamber of an electrolytic suppressor. Such an electrolytic suppressor is similar to the one described in FIG. 2 of U.S. Pat. No. 6,610,546, incorporated by reference. Preferably, the anode chamber and cathode chamber of this type of electrolytic suppressors are not adjacent to each other. When the suppressor is operated for anion analysis in an ion chromatography system with eluent recycle, the detector effluent flows from the anode chamber to the cathode chamber. As the anode chamber effluent flows through the electrochemically reducing cathode chamber, the reactive or oxidative species such as ozone and sodium percarbonate in the anode effluent are electrochemically reduced to non-oxidative species. Thus, the concentration of the reactive or oxidative species in the final suppressor effluent is reduced significantly. The use of this type of suppressor improves the performance of ion chromatography systems with eluent recycle.

Figure 5:
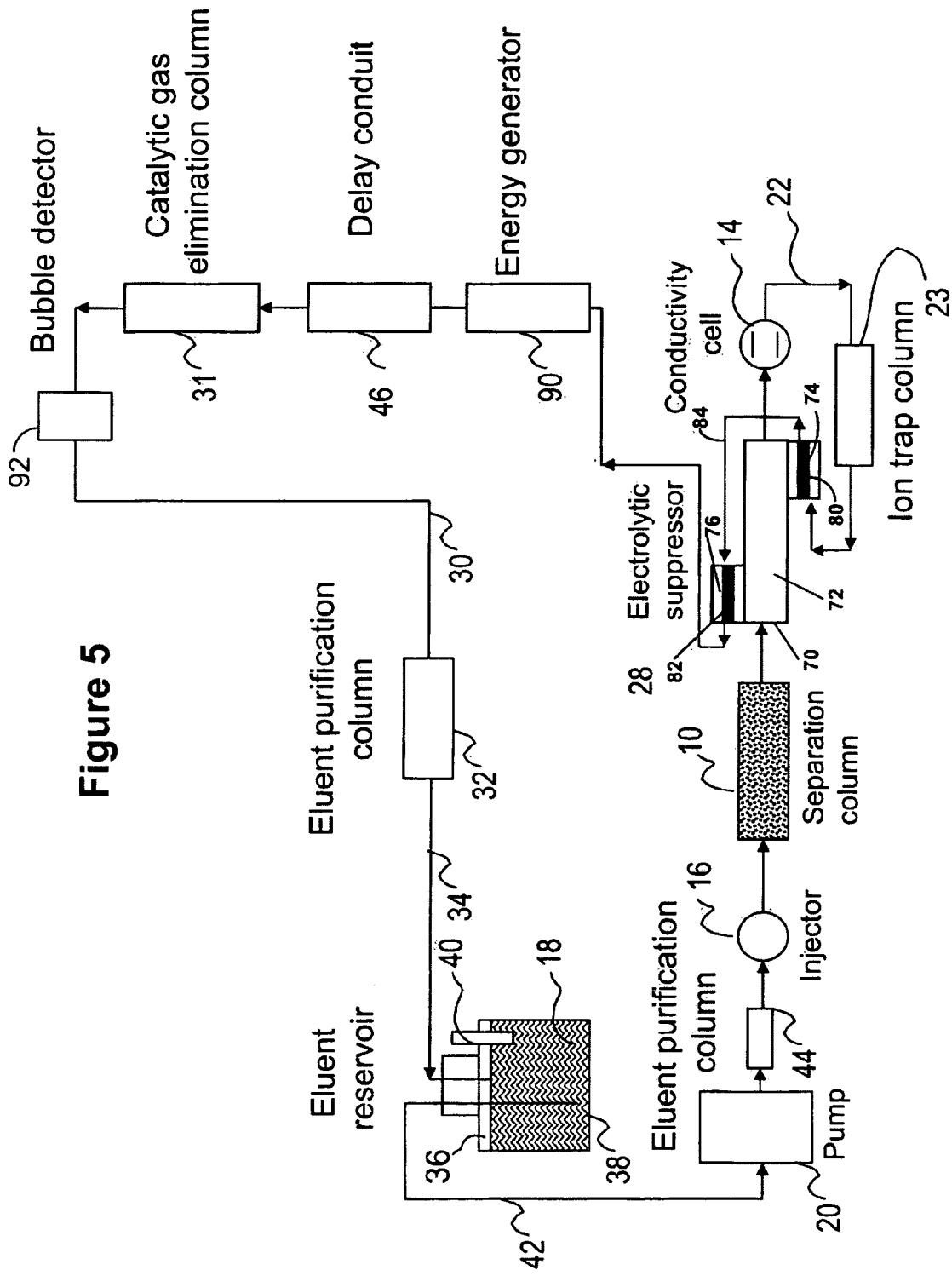

FIG. 5 shows another embodiment of the present invention. Like parts with FIG. 4 with be designated with like numbers. In this embodiment, an energy generator 90 is disposed between the outlet of suppressor 70 and catalytic gas elimination column 31. As illustrated, it is disposed between suppressor flow channel 76 and the inlet of delay conduit 46. In some applications, the delay conduit 46 can be eliminated and so flow will go directly to column 31. The energy can be irradiation, as by UV light, heat or some other energy source. For irradiation, the energy generator may be a reaction coil including a UV light source, such as a high pressure mercury lamp since the decomposition of ozone in the aqueous solution is known to be accelerated by using ultraviolet irradiation. The energy source may also be heat to accelerate the decomposition of ozone in the suppressor regenerant channel effluent. The half-life of ozone in the aqueous solution (pH 7) is known to decrease from about 20 minutes to about 8 minutes when the temperature is increased from 20° C. to 35° C.

FIG. 5 also illustrates a gas bubble detector 92 downstream of catalytic gas elimination column 31 which can be used in any of the systems described. A number of detection methods including optical and electrical measurement techniques may be applied to detect the presence of gas bubbles in a flowing liquid stream. The function of the gas bubble detector is to ensure the safe operation of the system in case the catalytic gas elimination column malfunctions. If the catalytic gas elimination column malfunctions and fails to recombine hydrogen and oxygen gas in the suppressor effluent, hydrogen gas may accumulate in the eluent reservoir to a level that present a explosion risk. To minimize or eliminate this risk, this embodiment uses a gas bubble detector to monitor if the eluent recycled back to the eluent reservoir contains gas bubbles. If an excessive volume of gas in the recycled eluent is detected, the gas bubble detector can be designed to provide a signal to power down the pump and turn off the electric current to the electrolytic suppressor in an ion chromatography system with eluent recycle to ensure its safe operation.

It is also possible to recycle ion chromatography eluent containing an organic solvent as long as the solvent is electrochemically stable.

Figure 6:
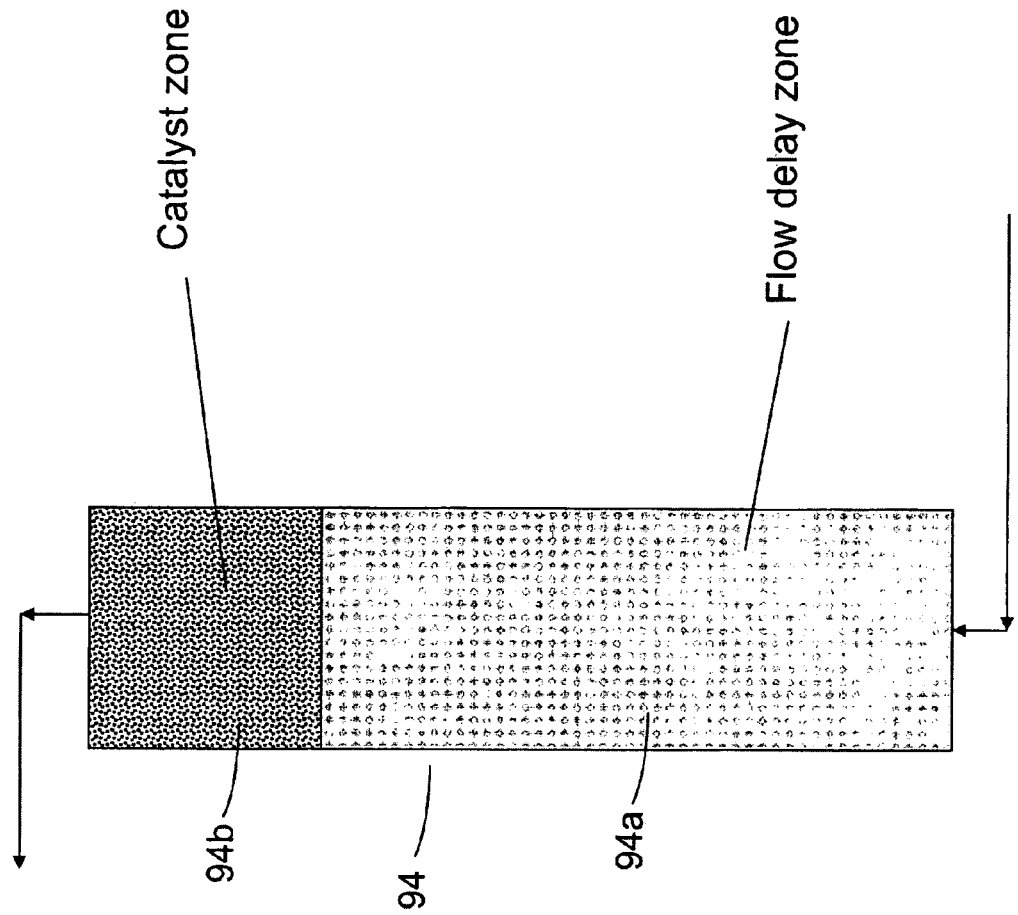

In another embodiment, as shown in FIG. 6, delay conduit 46 and catalytic gas elimination column 31 can be combined in a singled column device or housing. For example, referring to FIG. 6, column 94 includes an upstream zone or compartment 94a which is part of the delay conduit. Compartment 94a may be filled with packing, e.g. inert micro pellets or beads, or may take one of the other forms of delay conduit discussed above. The downstream, compartment 94b (the upper compartment as illustrated) is the catalyst zone, e.g. of the type described for column 31, in fluid communication with the column outlet.

Figure 7:
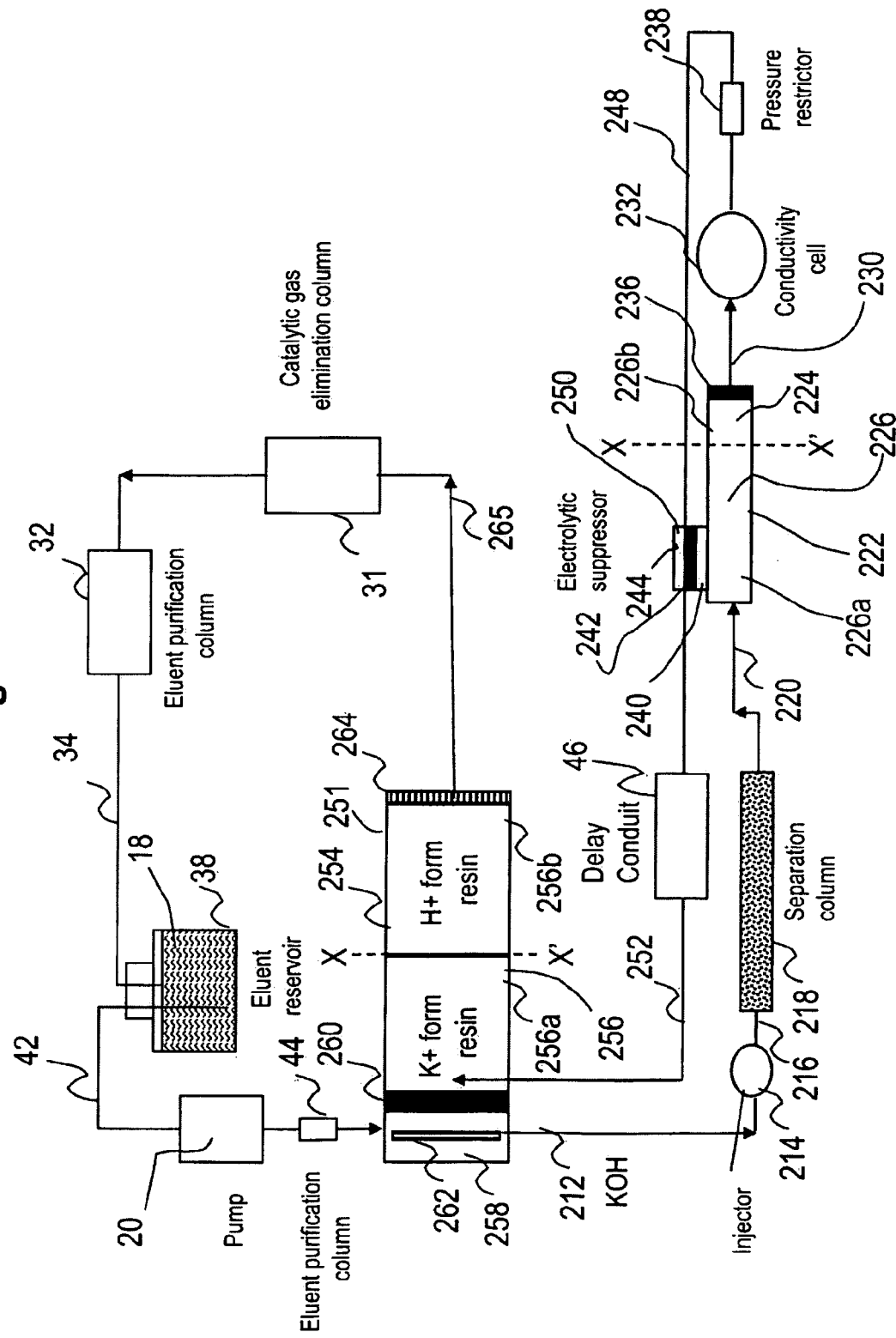

Referring to FIG. 7, an ion-reflux based chromatography system using water recycle is illustrated using the principles and the same system as FIG. 2 of U.S. Pat. No. 7,329,346 with the addition of a delay conduit 46 as described herein. The description of FIG. 2 of the '346 patent is incorporated by reference. Like parts with FIG. 1 herein will be designated with like numbers in FIG. 7.

The system of FIG. 7 illustrates the combined use of water purification columns and the catalytic gas elimination column for recycling water in an ion-reflux based ion chromatography system that generates and recycles potassium hydroxide eluents for anion analysis. In this ion chromatography system, the deionized water is used as the preferred carrier stream in the electrolytic generation and recycle of potassium hydroxide eluent. The effluent from the outlet of the eluent generation and recycle module is a mixture of water, hydrogen gas, oxygen gas, and possibly some trace components derived from the operations of the entire ion-reflux based ion chromatography system. To recycle the water, the effluent from the eluent generation and recycle module is first passed through the catalytic gas elimination column to eliminate hydrogen and oxygen gases. Since stoichiometric amounts of hydrogen and oxygen gases are generated in the electrochemical processes occurring in the electrolytic eluent generation and recycle module and the electrolytic suppressors, it is expected that hydrogen and oxygen combine to form water in the same amount that is originally consumed. The effluent from the catalytic gas elimination column is then passed through the water purification column to remove the remaining trace ionic and nonionic contaminants. The purified water is routed back to the water reservoir.

Referring specifically to FIG. 7, the solution leaving the eluent generator 251 in line 265 flows through catalytic gas elimination column 31, through an eluent purification column 32 through line 34 into container 38 for eluent reservoir 18. The recycled solution in line 34 is mixed in eluent reservoir 18 and is directed via pump 20 in line 42 through a second eluent purification column 44. A vent port in reservoir 18 is not illustrated because hydrogen and oxygen gases may be eliminated in column 31. From there on, the system is as described above.

Referring again to FIG. 7, an ion chromatography system is illustrated using a continuous electrolytically regenerated packed bed suppressor (CERPBS) form of suppressor and one embodiment of the eluent generator. The system includes an analytical pump 20 connected by tubing 212 to sample injection valve 214 which in turn is connected by tubing 216 to a flow-through chromatographic separator 218 typically in the form of a chromatographic column packed with chromatographic resin particles. The effluent from chromatographic column 218 flows through tubing 220 to a packed ion exchange resin bed flow-through suppressor 222. Typically, suppressor 222 is formed of a column 224 packed with an ion exchange resin bed 226 of the type used for ion chromatography suppression. Electrodes are spaced apart in the suppressor, with at least one electrode separated from the resin by a barrier described below. The electrodes are connected to a direct current power supply, not shown. The configuration is such that with an aqueous stream flowing through the suppressor and the application of power, water in the aqueous stream is electrolyzed to form a source of hydronium ion or hydroxide ion to continuously regenerate the ion exchange resin bed during the analysis.

The suppressor effluent is directed through tubing 230 to a suitable detector 232 and then eventually to waste. A preferred detector is a conductivity detector with a flow-through conductivity cell. The chromatography effluent flows through the cell.

Suppressor 222 generates hydronium ions (and oxygen gas) at the anode and hydroxide ions (and hydrogen gas) at the cathode. That is, a water-containing eluent solution including electrolyte is directed from the pump and through tubing 212. Sample is injected through sample injection valve 214, and is directed by tubing 216 into chromatographic column 218 to form a first chromatography effluent including separated ionic species of the sample. For simplicity of description, unless otherwise specified the system will be described with respect to the analysis of anions using an eluent solution including sodium hydroxide as the electrolyte.

A suitable sample is supplied through sample injection valve 214 which is carried in a solution of eluent supplied from pump 20. Anode 236 is disposed at the outlet end of resin bed 226 in intimate contact with the resin therein. The effluent from bed 226 is directed to a detector suitably in the form of a flow-through conductivity cell 232 of the conductivity detector (not shown), for detecting the resolved anions in the effluent, connected to a conductivity meter.

The system also includes an optional component for pressurizing the effluent from suppressor 222 prior to detection to minimize adverse effect of gases (hydrogen or oxygen) generated in the system as will be described hereinafter. Such pressurizing means comprises a pressure restrictor 238 downstream of conductivity cell 232 to maintain the ion chromatography system under pressure.

Column 224 is typically formed of plastic conventionally used for an ion exchange column. It has a cylindrical cavity of a suitable length, e.g., 60 mm long and 4 mm in diameter. It is packed with a high capacity cation exchange resin, e.g., of the sulfonated polystyrene type. The resin is suitably contained in the column by a porous frit which serves to provide an outlet to the column. In the illustrated embodiment, the porous frit is porous electrode 236 which serves the dual function of containment of the resin and as an electrode.

A barrier 240 separates bed 226 from electrode 242 in the interior of a hollow housing defining an ion receiving flow channel in electrode chamber 244 preventing any significant liquid flow but permitting transport of ions only of the same charge as the charge of exchangeable ions on resin bed 226. For anion analysis, barrier 240 is suitably in the form of a cation exchange membrane or plug separating electrode chamber 244 from the cation exchange resin.

A conduit 248 is provided to direct the aqueous liquid stream to the inlet 250 of electrode chamber 244. Conduit 252 takes the effluent from chamber 244 to the eluent generator 251. This provides a means of making electrical contact with the electrodes that is at the same time easy to seal against liquid leakage.

The line X-X is illustrated across the resin bed 226. For reasons which will be explained below, the resin upstream of the dotted line may be predominantly or completely in the form of the cation counter ion of the base used as the electrolyte during separation. Downstream of the line X-X, the resin may be predominantly or completely in the hydronium form. The line X-X represents the interface.

For anion analysis, a polarizing DC potential is applied between cathode 242 and anode 236, and the following reactions take place.

The water is electrolyzed and hydronium ions are generated at anode 236 according to the following reaction:

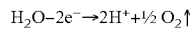

This causes cations in the cation exchange resin bed 226 to migrate to barrier 240. This, in turn, displaces hydronium ions upwardly through bed 226 which causes a similar displacement of cations ahead of them. The cations electromigrate toward the barrier 240 to be transported across the barrier 240 toward cathode 242 in cathode chamber 244 while water is electrolyzed at cathode 242 to generate hydroxide ions according to the following reaction:

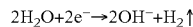

The cations which have transported across the barrier combine with the generated hydroxide ions to form cation hydroxide in cathode chamber 244. The effluent from separator bed percolates through the cation form resin in inlet bed section 226 until it reaches the hydronium form resin in bed section 226 where it is neutralized while the cation is retained on the resin. At this point, the anion salts are converted to their respective acids and the cation hydroxide is converted to weakly ionized form, water.

The suppressed effluent liquid containing the separated anions leaves bed 226 through conduit 230 and passes to conductivity cell 232 in which the conductivity of the separated anions is detected.

The suppressor of FIG. 7 has been described with respect to a system for the analysis of anions. However, the system is also applicable to the analysis of cations. In this instance, electrode 236 is a cathode and electrode 242 is an anode. The ion exchange type of resin is reversed. Thus, the resin in separator bed 218 is a cation exchange resin and the resin in suppressor bed 226 is an anion exchange-resin. The plug or membrane 240 is made of an anion exchange material.

Briefly described, the suppressor works as follows for the cation analysis. The aqueous liquid stream containing cations to be detected and an acid electrolyte aqueous eluent are directed through separator bed 218 including cation exchange resin. The effluent from separator bed 218 flows through suppressor bed. 226 including anion exchange resin with exchangeable hydroxide ions. The acid in the eluent. is converted to weakly ionized form. Some of the exchangeable hydroxide is displaced by anions from the acid.

An electrical potential is applied between the cathode 236 and anode 242. Water is electrolyzed at electrode 236 to generate hydroxide to cause anions on the anion exchange resin bed to electromigrate toward barrier 240 to be transported across the barrier toward the positively charged anode 242 in the ion receiving flow channel in electrode chamber 244 while water in chamber 244 is electrolyzed to generate hydronium ions which combine with the transported anions to form acid in the electrode chamber 244. The effluent liquid from the suppressor bed 226 flows past detector 232 in which separated cations are detected and is recycled to electrode chamber 244.

Referring again to FIG. 7, one embodiment of the eluent generator 251 is illustrated, describing first the system for anion analysis in which a base generated in electrode chamber 244 is directed to the eluent generator 251. This embodiment is analogous in electrochemical operation to suppressor 224. In this embodiment of the eluent generator, a suitable housing 254 contains an electrolyte ion reservoir in the form of a packed bed of ion exchange resin 256. Resin bed 256 is separated from a first generator electrode chamber 258 by a charged generator barrier 260 which prevents significant liquid flow but permits transport of electrolyte ions and thus may be of the type described with respect to suppressor barrier 240. A generator electrode 262 is disposed and enclosed in generator electrode chamber 258 and may be of the same type of construction as electrode chamber 244. At the opposite side of barrier 260 from electrode 262 is flow-through generator electrode 264 analogous in function and structure to suppressor electrode 236.

The electrochemical reactions described above with respect to the suppressor occur in the eluent generator and so are incorporated herein by reference. Thus, for analysis of anions, the line x-x separates the inlet section 256a from the outlet section 256b of resin bed 256. The feed stream in line 252 flows into inlet section 256a in the cation form while the outlet section is in the hydronium ion form. However, one difference is that the feed stream in conduit 252 already includes base. The feed stream exits packed resin bed 256 adjacent barrier 260 and flows across bed 256 and out the outlet through electrode 264 or past some other form of electrode as described above. Similarly, the packed bed includes resin in the electrolyte ion form (e.g., potassium or sodium) at its inlet end adjacent barrier 260 and in hydrogen ion form near the outlet end adjacent electrode 264.

The same type of packed bed resin or other form of matrix may be used in the eluent generator as in the suppressor. As illustrated, the source of aqueous liquid flowing through generator electrode chamber 258 can be liquid recycled from the outlet of the resin bed chamber 254. Specifically, such liquid flows through conduit 265 and into a mixed (cation and anion exchange) bed water polishing column, or eluent purification column 32. This column is typically 2 to 40 cm in length and 0.5 to 10 cm in internal diameter. From there, the stream flows through conduit and flows to eluent reservoir 18. In the case of anion analysis, the cation hydroxide is generated in chamber 258 adjacent the cathode. in the manner described above with respect to the suppressor. The water source after passing through the water polisher is deionized and so does not interfere with the analysis. An optional eluent purification column 44 may be placed after pump 20 to further purify the deionized water stream.

Delay conduit 46 is disposed between suppressor 224 and eluent generator 251. An advantage of this location is that the unstable oxidative compounds that could be detrimental to the catalyst and/or ion exchange medium in column 31 could also be detrimental to the ion exchange medium in eluent generator 251. Thus, the delay in conduit 46 can reduce the harmful effect of such compounds. However, the delay conduit can be disposed in other locations such as between cell 232 and column 31, preferably between suppressor 224 and column 31.

It is useful to discuss the principles of operation of a catalytic gas elimination chamber typically contained in a flow-through housing termed a column herein. Even though the combination of hydrogen and oxygen to form water is an exothermic process, hydrogen and oxygen do not react automatically when mixed together. The reason for this is the relatively large activation energy needed to begin the reaction. The mechanism is somewhat complex. It is a free radical mechanism with one of the initiation steps is:

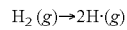

$$H_2(g) \rightarrow 2H\cdot(g)$$

Breaking the bond between the two hydrogen atoms requires 432 kJ/mole. This energy can be initially provided by a spark or a flame. After the reaction begins, the produced energy provides the necessary energy to continue breaking apart the hydrogen molecules. A catalyst provides an alternative mechanism that has a lower activation energy, this allows the reaction to proceed without the requirement of the initial addition of energy such as a flame or spark.

According to the invention, preferred metal catalysts in catalytic gas elimination column 31 include one or more metals from the Platinum group. Such Platinum group metals are defined herein to include, in order of increasing atomic weights, ruthenium, rhodium, palladium, osmium, iridium and platinum. Such metal catalysts could be used separately or in combination or could be incorporated in an alloy, for example, a platinum nickel alloy. The invention will first be described with respect to platinum metal catalysts.

Platinum is known to catalyze the reaction of hydrogen and oxygen. (Nature, vol. 390, 495-497, 1997; Journal of Chemical Physics, vol. 107, 6443-6447, 1997; Surface Science, vol. 324, 185-201, 1995.) If platinum is placed into a container filled with hydrogen and oxygen, the platinum begins to glow as it heats up, and water droplets condense in the container. Cooling the platinum so that it doesn't just ignite the mixture provides a smooth conversion of the hydrogen and oxygen to water. This reaction occurs because platinum provide a new route for the reaction. In this new pathway, hydrogen molecules react with the platinum atoms on the surface of platinum. This reaction breaks the H-H bond and forms two Pt-H bonds. The energy of activation for this process is small. Oxygen reacts with these Pt-H groups to form water, again, with a very small energy of activation. Through this low energy route for the reaction, platinum catalyzes the recombination of oxygen and hydrogen gases. The term "catalyst" encompasses any catalyst that performs this function. Platinum is described as one specific example of such a catalyst.

The above principles of using the known property of a catalyst such as platinum to catalytically induce the reaction between hydrogen gas and oxygen gas to form water provide the basis for the catalytic gas elimination chamber of the present invention for use in liquid chromatography. This permits the elimination of these gaseous electrolysis byproducts of an electrolytic suppressor in the eluent in a system like FIG.

1. In such a system, the effluent from the outlet of the electrolytic suppressor regenerant chamber 24 is passed through the catalytic gas elimination column 31, where the hydrogen and oxygen present in the effluent react catalytically to form water. Column 31 may be packed with a suitable catalyst such as pure Pt in metal particle, mesh, or foil form. Alternatively, the column may also be packed with other inert substrates coated with Pt. In the present invention, optional catalytic gas elimination column 31 serves several important functions. First, it provides an elegant means to conveniently eliminate the build up hydrogen and oxygen gases and thus facilitates the operation of continuous eluent recycle. Second, the water-forming reaction of hydrogen and oxygen is expected to be stoichiometric in the column, and the amount of water formed is expected to be in principle the same as the amount of water that is originally consumed to produce hydrogen and oxygen gases in the electrolytic operation of the suppressor. In principle, this feature eliminates an increase in the concentration of eluent due to the consumption of water in the electrolytic operation of the suppressor. Third, the Pt catalytic gas elimination column also serves the function to catalytically decompose trace levels of hydrogen peroxide which may be formed during the electrolytic operation of the suppressor. The presence of hydrogen peroxide in the recycled eluent is potentially detrimental since it may attack the ion exchange functional groups in the separation column and the eluent purification column in the system and degrade the column performance. The use of Pt to catalyze the decomposition of hydrogen peroxide is well known (Bull. Korean Chem. Society, 1999, vol. 20(6), 696; U.S. Pat. No. 6,228,333).

The catalytic gas elimination chamber may have a wide variety of physical forms. One embodiment uses a chromatographic column housing with fritted flow-through end fittings that are used to retain either pure Pt metal particles, mesh, or foils packed inside the column. The column may also be packed with other inert substrates coated with Pt. In a preferred embodiment, the internal diameter of the column is 0.1 mm or larger and the length of the column is 0.5 cm or longer. It is preferred to use Pt packing material in forms that provide high surface area to increase its catalytic efficiency. It is also preferred to operate the catalytic gas elimination chamber in flow rates ranging from 0.1 uL/min to 50 mL/min although other flow rates may be used.

Another embodiment relates to a catalytic gas and ionic species removal device ("the CGISRD"). It is particularly useful in a chromatography system, particularly the ion chromatography systems disclosed herein. In general, the device includes a liquid flow-through housing, a Platinum group metal catalyst for catalytically combining hydrogen and oxygen gases, or for catalytically decomposing hydrogen peroxide, or both, disposed in a housing, and flow-through ion exchange medium also disposed in the housing. In preferred embodiments, the Platinum group metal catalysts are platinum, palladium, or mixtures thereof, in sole metal or alloy form. As set out herein, the Platinum group metal catalysts may also include ruthenium, osmium, rhomium, and iridium, in substantially pure metals form or in an alloy form.

The CGISRD can be formed as a flow-through housing of the type described herein regarding catalytic gas elimination column 31 in FIG. 1. However, in addition to the Platinum group metal catalyst, the CGISRD includes flow-through ion exchange medium disposed in the housing. Suitable flow-through ion exchange medium may include an ion exchange particulate bed or an ion exchange monolith, such as described in U.S. Pat. No. 7,074,331. In some embodiments, the metal catalyst is not bound to the ion exchange medium. Here, the ion exchange medium can be disposed upstream or downstream of the metal catalyst or can be mixed with the metal catalyst. An advantage of this approach is that it eliminates the need for having a separate column containing the ion exchange phase for removing analyte ions, counterions or both and having a separate column for the metal catalyst, thus lowering the overall cost of the hardware required for this work. Additionally having a single column enclosure minimizes the number of fittings and tubing connections.

In a preferred embodiment of the CGISRD, the Platinum group metal catalysts is irreversibly bound as a coating to said ion exchange medium, as by electrostatic binding. The device has sufficient ion exchange capacity for ion exchange with ions, such as sample ions or sample counterions, in a flowing liquid stream so that a substantial amount of, preferably most or all of, such ions are bound for removal from the flowing liquid prior to recycle to the separation medium as is performed in eluent purification column 32 of FIG. 1 to the ion exchange medium. Such ion exchange capacity may be partially or completely provided by the coated ion exchange medium by providing excess ion exchange capacity in the medium which is not consumed by irreversible binding to the coating. Thus, when removal of such ions is performed by the coated ion exchange medium, the excess capacity of the ion exchange phase of the catalyst coated ion exchange material that is available for the removal is preferably more than 0.1 times, more preferably 0.3 times and most preferably 0.5 times or more of the capacity of the uncoated ion exchange phase. Such ion exchange capacity can be supplemented by adding uncoated ion exchange medium to the coated ion exchanger medium in the device. This added ion exchange capacity would aid improved removal of sample ions or sample counter ions.

In one embodiment the metal catalyst is bound to the ion exchange medium by using the metal in a reagent which includes ionic moieties which irreversibly bind electrostatically to the ion exchange moieties on the ion exchange medium. Suitable metal catalyst reagents for attaching to ion exchange resins are metal compounds, preferably metal-containing amine cations for attaching to the cation exchange resins or metal-containing chloro-compounds that are metal-containing anions for attaching to anion exchange resins. The reagents preferably would be electrostatically bound to the ion exchange moieties before they are permanently attached to the surface. Such reagents include tetraammineplatinum (II) chloride, diamminepalladium (II) nitrite, sodium hexachloro palladate (IV), sodium hexachloro platinate (IV) ammonium pentachloroaquo rhodate (III), potassium pentachlororhodate (III), pentamminechlororhodium(III)dichloride, ammonium pentachloroaquo ruthenate (III), hexaammine ruthenium (III) chloride, ammonium hexachloro iridate, (III), potassium hexachloro iridate (IV), potassium hexachloro osmate (IV) and the like. Such reagents could be used separately or in mixtures for coating various catalyst metals on top of the ion exchange materials. For example, two or more reagents could be mixed and electrostatically bound to the cation exchange resin phase in varying ratios. This would yield phases with a mixed catalyst containing surface. For example, the combination of platinum and palladium in a coated phase yields excellent catalytic decomposition of hydrogen peroxide in addition to good catalytic formation of water from the electrolytic gases. Thus, the catalyst coated materials could be tailored for a given application. In one coated embodiment, the metal catalyst is in a thin layer, preferably a monolayer, to minimize the total catalyst used. Also, after synthesis, it is possible to use a mixture of various catalyst coated ion exchange materials.

In a preferred embodiment, the Platinum group metal catalyst comprises both platinum and palladium. For example, the ion exchange resin could be coated individually in two separate synthesis steps with platinum and palladium, respectively, and then the resin phase is mixed together and packed into a column. This would yield a combination of a platinum and palladium coated phase. It should be noted that the two phases in the above embodiment could also be packed in separate layers in a two layer or multi layer embodiment without substantially mixing the two phases. In another embodiment the two metal catalyst reagents are intimately mixed together and are attached to the ion exchange resin in one synthesis step. This would yield a surface that would have both reagents and ultimately both metal catalysts on the surface of the ion exchange resins. Using some resin phases, it is also possible to coat the resin with one catalyst metal followed by another coating step with another catalyst metal.

For anion analysis, the preferred ion exchange medium is in the cation exchange form. The residual cation exchange capacity can be used for removing the counter ion cation to the analyte ion. For example when analyzing drinking water the counter ions are typically monovalent and divalent cations such as sodium, ammonium, calcium and magnesium. For cation analysis the preferred ion exchange medium is in anionic form to remove anion counterions to the sample cations.

As set forth above, the catalyst coated ion exchange medium can be mixed with uncoated substrate ion exchange medium for enhancing the retention of counterions. In applications where it is desired to remove both counterions and analyte ions, such as after electroelution separation of analyte ions discussed hereinafter, a mixture of the catalyst coated ion exchange medium and ion exchange medium of opposite charge as in or mixed bed of both charges may be used.

Suitable ion exchange materials are disclosed in the prior art and are commercially available from Dow Chemical Co. as cation exchange or anion exchange materials sold as Dowex Ion exchange resins, or from Rohm and Haas as Amberjet or Amberlite and the like. The ion exchange materials have ion exchange groups that could be modified as per the present invention with a catalyst metal coating.

It should also be noted that the synthesis of the disclosed materials can be done in bulk before packing it into columns or could be done insitu within columns. For cost and practical reasons the former is preferred over the latter.

The systems of all embodiments are also applicable to the generation of a base eluent with appropriate reversal of polarity of the reagents and charged components for anion analysis.

Figure 8:
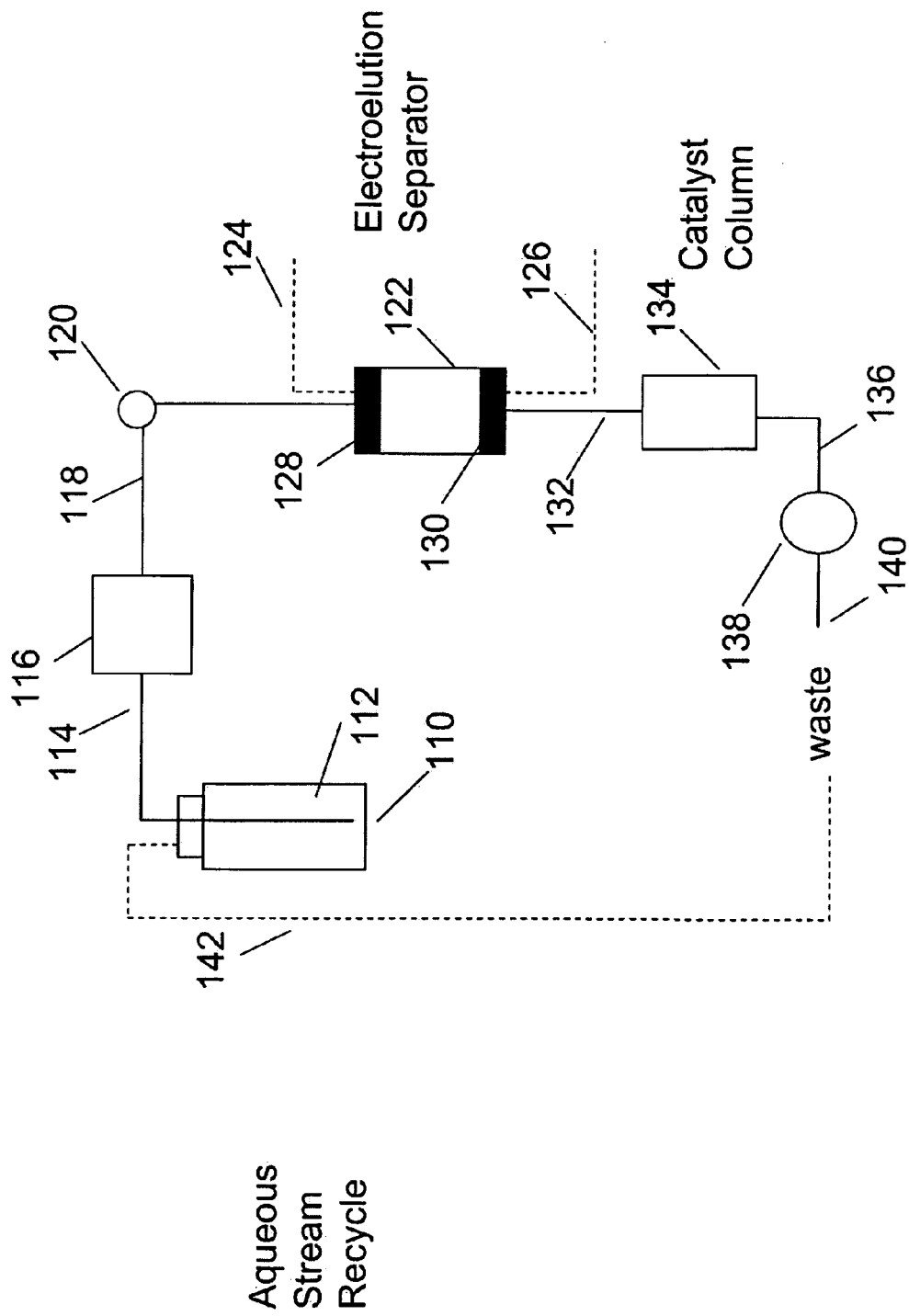

FIG. 8 illustrates a chromatography system using a catalytic gas elimination column and an electro elution separator column. An aqueous stream source container 110 with an aqueous source 112 is connected fluidically to a pump 116, which is connected to an injection valve 120 by conduit 118. This portion of the plumbing is similar to ion chromatography systems of the prior art. The injection valve is then plumbed to a chromatography separator 122 as in the prior art. The separator column 122 is packed with appropriate separator medium (not shown). Two flow-through electrodes 128 and 130 flank the ends the separation medium. The electrodes are connected to a power supply (not shown) via connectors 124 and 126. The fluidic line out of column 122 is connected to the inlet of catalytic gas elimination column 134 which may be built and operated as described for any of the embodiments herein. The outlet of catalytic gas elimination column is connected to a detector cell 138 (preferably a conductivity cell). The outlet of the cell 138 is diverted to waste 140 or routed back to the source container 110.

In operation, an aqueous stream, which may be water without an electrolyte, is pumped from container 110 and is routed via conduit 118 to injection valve 120. The stream is then routed out of valve 120 with or without the injected sample into separation column 122 for separating the individual components. Column 122 produces both hydrogen and oxygen gases are catalytically recombined back to water in catalytic gas elimination column 134 as described for any of the embodiments herein. In addition any peroxide is also decomposed according to the present invention. For the embodiment of FIG. 1 herein, in which ion exchange medium is not used in catalytic gas elimination column the analyte counter ions that are unretained in the column 122 may be removed in a purification column such as described for column 32 in FIG. 1. For catalyst column 134, which includes ion exchange medium as described herein, such ions may be removed in column 134. The sample ions are routed from catalyst column 134 and are substantially unimpeded into the detector cell 138 for detection. The aqueous stream is routed to waste 140 or could be recycled using conduit 142 back into the aqueous source stream container 110. One or more trap columns (not shown) could be installed in line 142 to remove the analyte ions or any neutral species.

Construction and operation of electro elution separator 122 may be accomplished as described in U.S. Pat. No. 6,093,327, particularly columns 11-18, incorporated herein by reference. In this system, the eluent can be an aqueous liquid such as deionized water, or an acid, base, or salt-containing aqueous solution.

In another embodiment (not shown), catalytic gas elimination column 134 could be installed after the detector cell 38. In this embodiment some backpressure is preferred to compress the electrolytic gases to aid detection. Column 134 in this embodiment would allow the catalysis reaction, coupled with aiding the decomposition of peroxide and in addition aiding the removal of analyte ions or counterions or both. In this embodiment the aqueous stream is routed via conduit 142 back into the aqueous source stream container 110. A trap column (not shown) could be installed in line 142 to remove any neutral species. In addition a purifier column could be used to purify the aqueous stream in line 114 or line 118.

In the above embodiments of the present invention, water formed by the catalytic combination of hydrogen and oxygen gas can serve as a source of water for the eluent stream by flowing the produced water into the eluent stream. The gases can be electrolytically generated in the chromatography system or supplied from independent sources of hydrogen and oxygen gas such as from pressurized containers.

The following examples demonstrate the present invention for systems in which the eluents are prepared off-line and recycled and water is used in the electrolytic eluent preparation in ion chromatography.

Example 1. Ion chromatographic separation of common anions using an electrolytic suppressor and recycle of a sodium carbonate/sodium bicarbonate eluent.

This example illustrates the use of the eluent-recycle ion chromatography system shown in FIG. 1 for determination of common anions including fluoride, chloride, nitrate, phosphate and sulfate. A Dionex ICS-2000 ion chromatography system consisting of a dual-piston high pressure pump, a six-port injector, a column oven, and a conductivity detector was used. A Dionex 4-mm AS22 column (4 mm×250 mm) was used as the separation column. A solution of 4.5 mM sodium carbonate and 1.2 mM sodium bicarbonate was used as the eluent, and the separation was performed at 1.2 mL/min. A Dionex ASRS-300 electrolytic suppressor was used in the experiments. A flow-through delay column (10 mm×250 mm) was used. The catalytic gas elimination column contains a cation exchange resin coated with Pt. The eluent purification columns (9 mm×85 mm) were packed with appropriate ion exchange resins. The analyte trap column (9 mm×50 mm) was packed with an aminated anion exchange resin.

Figure 9:
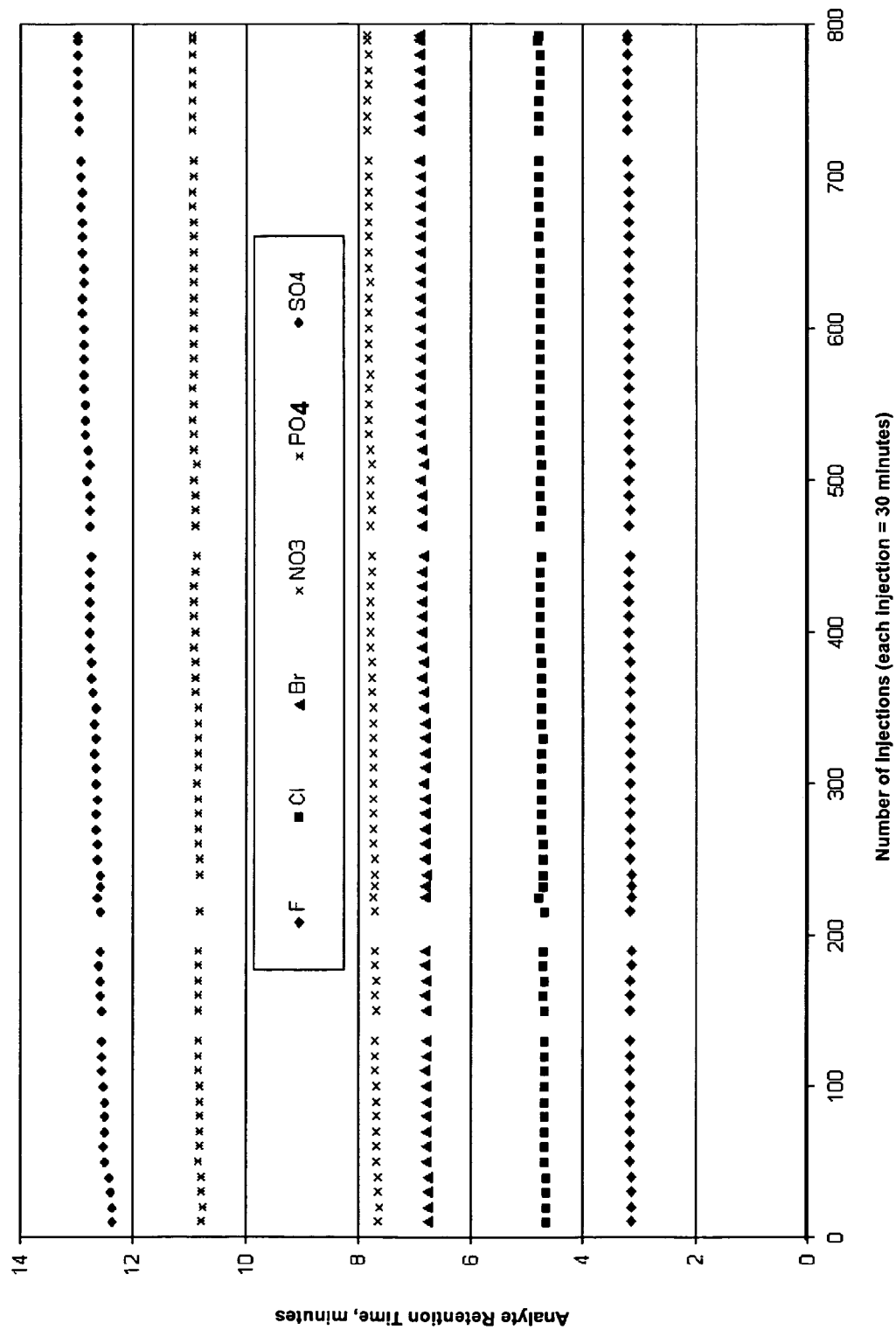
FIGS. 9-16 are graphs illustrating experimental results using the present invention.

In one set of experiments, sample solutions containing common anions such as fluoride, chloride, bromide, nitrate, phosphate, and sulfate were injected daily, the retention time of each analyte were monitored over a period of 400 hours during which a 4-liter solution of 4.5 mM sodium carbonate and 1.2 mM sodium bicarbonate was recycled continuously. If the eluent was not recycled, the total eluent consumption would have been 28.8 liters over the period of 400 hours. FIG. 9 shows the retention time reproducibility data obtained for the target analytes. The retention time percent RSD for the target analytes ranged from 0.48% for phosphate to 1.3% for sulfate over the period of 400 hours. These results indicate that the ion chromatography system shown in FIG. 1 can be used to perform reproducible separation of analyte ions of interest using recycled sodium carbonate eluent over an extended period of time. The operation of an ion chromatography system in such a format simplifies the system operations, minimize waste disposal, and reduce operating costs.

Example 2. Ion chromatographic separation of common cations using an electrolytic suppressor and recycle of a methanesulfonic eluent.

This example illustrates the use of an ion chromatography system with eluent recycle shown in FIG. 1 for determination of common cations including lithium, sodium, ammonium, potassium, magnesium, and calcium. A Dionex ICS-2000 ion chromatography system consisting of a dual-piston high pressure pump, a six-port injector, a column oven, and a conductivity detector was used. A Dionex 4-mm CS12A column (4 mm×250 mm) was used as the separation column, a solution of 20 mN methanesulfonic acid was used as the eluent, and the separation was performed at 1.0 mL/min. A Dionex CSRS-300 electrolytic suppressor was used in the experiments. A flow-through delay column (10 mm×250 mm) was used. The catalytic gas elimination column contains a cation exchange resin coated with Pt. The eluent purification columns (9 mm×85 mm) were packed with appropriate ion exchange resins. The analyte trap column (9 mm×50 mm) was packed with a fully sulfonated cation exchange resin.

Figure 10:
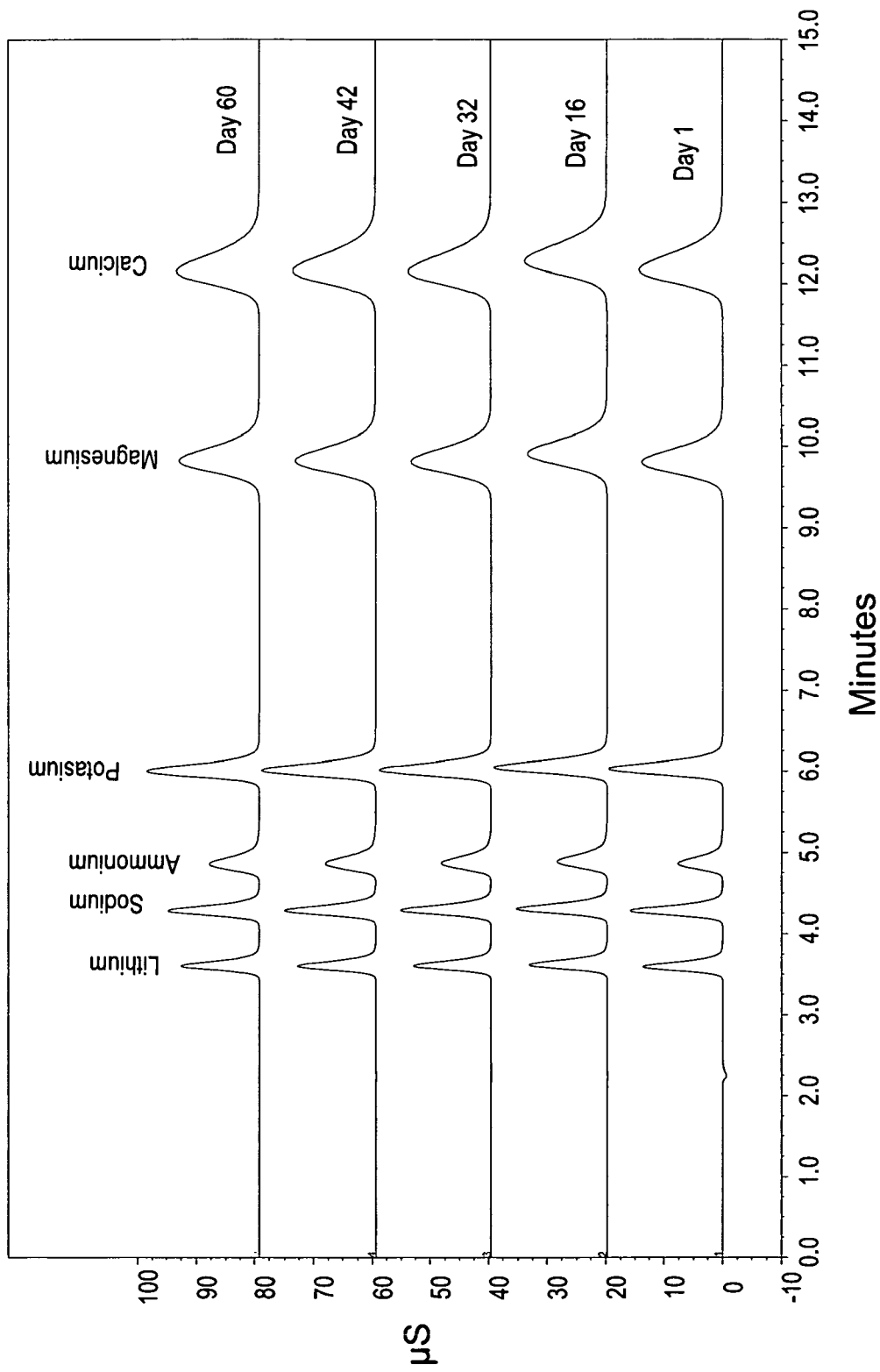

In one set of experiments, sample solutions containing lithium, sodium, ammonium, potassium, magnesium, and calcium was injected daily, the retention time of each analyte were monitored. FIG. 10 shows the representative -separations of six cations over the period of 60 days. These results indicate that the ion chromatography system shown in FIG. 1 can be used to perform reproducible separation of cations of interest over an extended period of time. The operation of an ion chromatography system in such a format simplifies the system operations, minimize waste disposal, and reduce operating costs.

Example 3: This example describes a process of preparing a platinum coated resin for this application. A cation exchange resin (commercially available from various resin manufacturers such as Rohm and Haas; Dow Chemicals etc) was used as the substrate. 100 g of the resin was converted to the sodium form using 1 M sodium hydroxide. Next the resin was washed with DI water and filtered. The resin was added to a 2 L bottle and the appropriate catalyst solution (For example Tetraammineplatinum (II) Chloride solution) app. 630 ml at a concentration of 4000 mg/L was added. The bottle was capped and tumbled to mix the resin intimately with the catalyst solution for 2 hours. The resin was washed and filtered. At this point a layer of platinum is adhered to the resin by electrostatic means. Next, a 5% borohydride solution was made and the resin was placed in this container and mixed with care. The container is left open to ambient environment (due to bubbling in the container) and placed in an oven at 65° C. for 4 hours. After 4 hours the resin was filtered and washed with DI water for four times to remove all the reactants. The resin appears blackened and is now ready for catalytic operation.

Example 4. A 10 um resin (Ethylvinylbenzene 55% cross linked with divinylbenzene) was used as the substrate in this experiment. The resin was coated with a) 4000 mg/L Tetraammineplatinum (II) Chloride solution 2) 4000 mg/L Diamminepalladium (II) nitrite solution and 3) A combination of 1) and 2) at a concentration of 2000 mg/L each. The resin synthesis protocol followed the outline listed above in example 3. Three standard chromatography guard columns from Dionex Corporation with a 9×50 mm dimensions were packed with the above coated resins using DI water as the packing media.

The columns were tested for peroxide removal using a DX600 IC system with an electrochemical detector from Dionex Corporation, Sunnyvale, Calif. A CP PA20 column was used with an eluent comprising 100 nM NaOH at 0.5 ml/min flow rate and at 30° C. A gold electrode was used as the electrode and detection was pursued with a pre-loaded quadruple waveform with AgCl reference electrodes. A 10 μL injection sample loop was used in this work. For testing the catalytic function an optical sensor was used to detect the transition of the bubble. A voltage response to the transition of the bubble was recorded. It should be noted that this setup would detect all bubbles and any bubbles originating from leaking fittings etc would also be detected. Therefore care was exerted to keep all the fittings finger tight and leak free. The voltage signal from the bubble-detector was fed to a UI 20 interface module from Dionex Corporation and the signals were collected using Chromeleon®, a Chromatography software from Dionex Corporation (Sunnyvale, Calif.). In the experimental setup a 4 mm ASRS suppressor from Dionex Corporation was pumped with 9 mM sodium carbonate eluent at a flow rate of 1 ml/min and the suppressor waste was diverted into a 9×50 mm catalyst column as per the present invention and the fluid eluting out was diverted into an ⅛ Teflon tubing on which was mounted an optical sensor for detection of bubbles. This setup as per the present invention was sufficient to monitor the transition of bubbles. The fluid eluting out of the ⅛" Teflon tubing was routed to a container or was directly routed to an injection valve for peroxide detection. In some cases a known standard amount of peroxide was pumped into the catalyst column and was routed to the injection valve for testing the peroxide removal efficiency.

Figure 11:
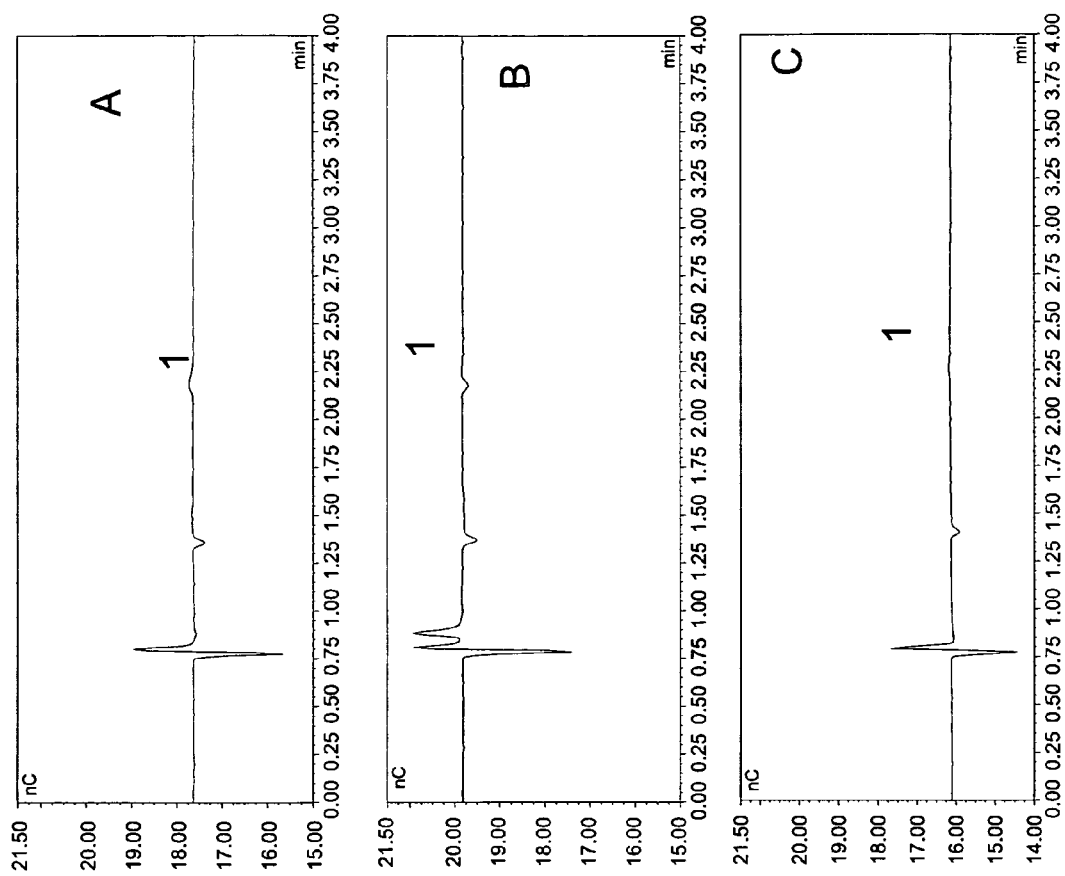

Example 5. FIG. 11 shows the peroxide removal efficiency of the devices. A 10 mg/L peroxide standard was used in this experiment and tested as per the setup discussed in example 4. Trace A in FIG. 11 showed the performance of a platinum coated ion exchange resin; trace B showed the performance of a palladium coated ion exchange resin and trace C showed the performance of a combination (palladium and platinum) coated resin. It is clear from the intensity of peak 1 that most of the peroxide was removed by the setup of trace C. All three traces showed significant removal of peroxide as apparent from the intensity of peak 1. The peak area for a standard run (not shown) was 4.084 and the three catalyst columns showed good removal efficiency for peroxide as shown in Table 1. Here the removal efficiency is expressed as a % of the control which has no catalyst resin.

TABLE 1

Peroxide removal results with a 10 um resin (Ethylvinylbenzene based and 55% cross linked with divinylbenzene)

| Catalyst Coating | Peak Area | Removal Efficiency % |
|---|---|---|
| None | 4.084 | |
| Palladium | 0.0063 | 99.85 |
| Platinum | 0.0139 | 99.66 |
| Palladium + Platinum | 0.0012 | 99.97 |

Figure 12:
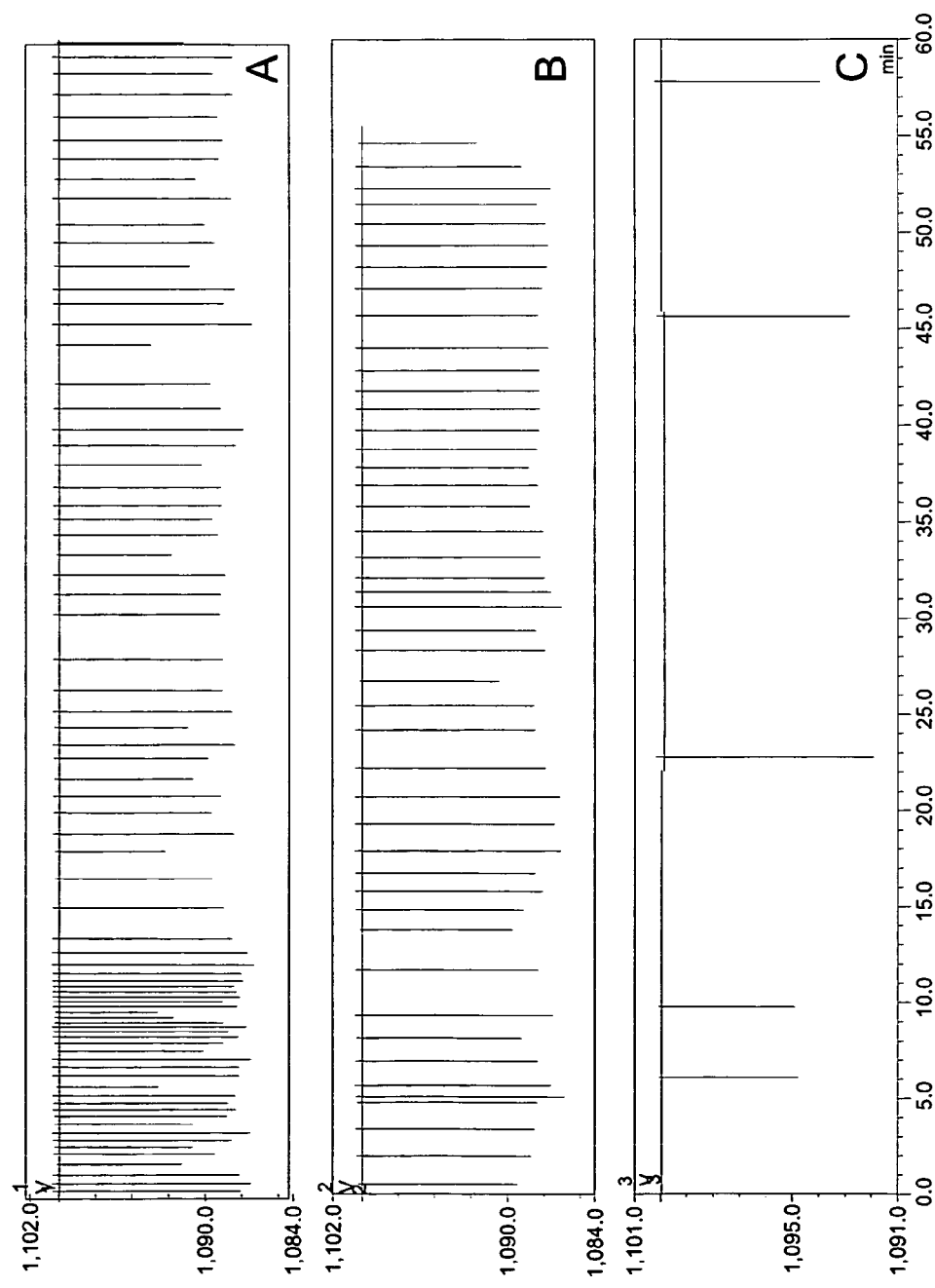

Example 6. FIG. 12 shows bubble removal comparison between the three tested columns. Bubbles here are detected as negative spikes of the voltage signal. The more the number of bubbles detected the poorer the catalyst function. Trace A, B & C display the performance of the three catalyst resins as discussed previously in Example 5. Excellent bubble removal is seen with a combination of Platinum and Palladium coated resin.

Figure 13:
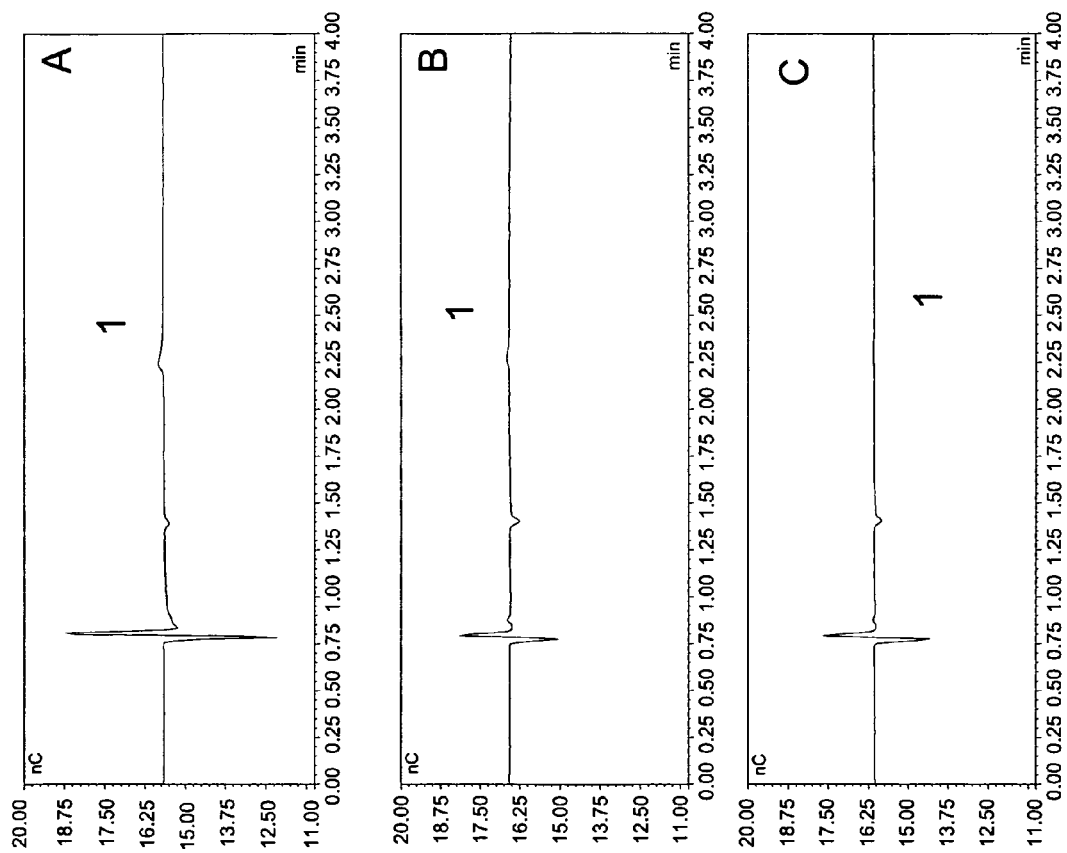

Example 7. Since the bubbles were not completely removed we investigated another resin for this application. This is a polystyrene divinylbenzene based proprietary resin from Dionex Corporation (Sunnyvale, Calif.) that was 2% cross-linked and had a diameter of 15.4 micron. This resin was coated with the three combinations as discussed above following the protocol described in Example 3. The peroxide removal is shown in FIG. 13 and shows once again the combination (trace C) outperforming the single metal coated resins. The results are summarized in Table 2 below.

TABLE 2

Peroxide removal results with a 15.4 um resin (Styrene based and 2% cross linked with divinylbenzene)

| Catalyst Coating | Peak Area | Removal Efficiency % |
|---|---|---|
| None | 5.03 | |
| Palladium | 0.0058 | 99.88 |
| Platinum | 0.0135 | 99.73 |
| Palladium + Platinum | 0.0016 | 99.97 |

Figure 14:
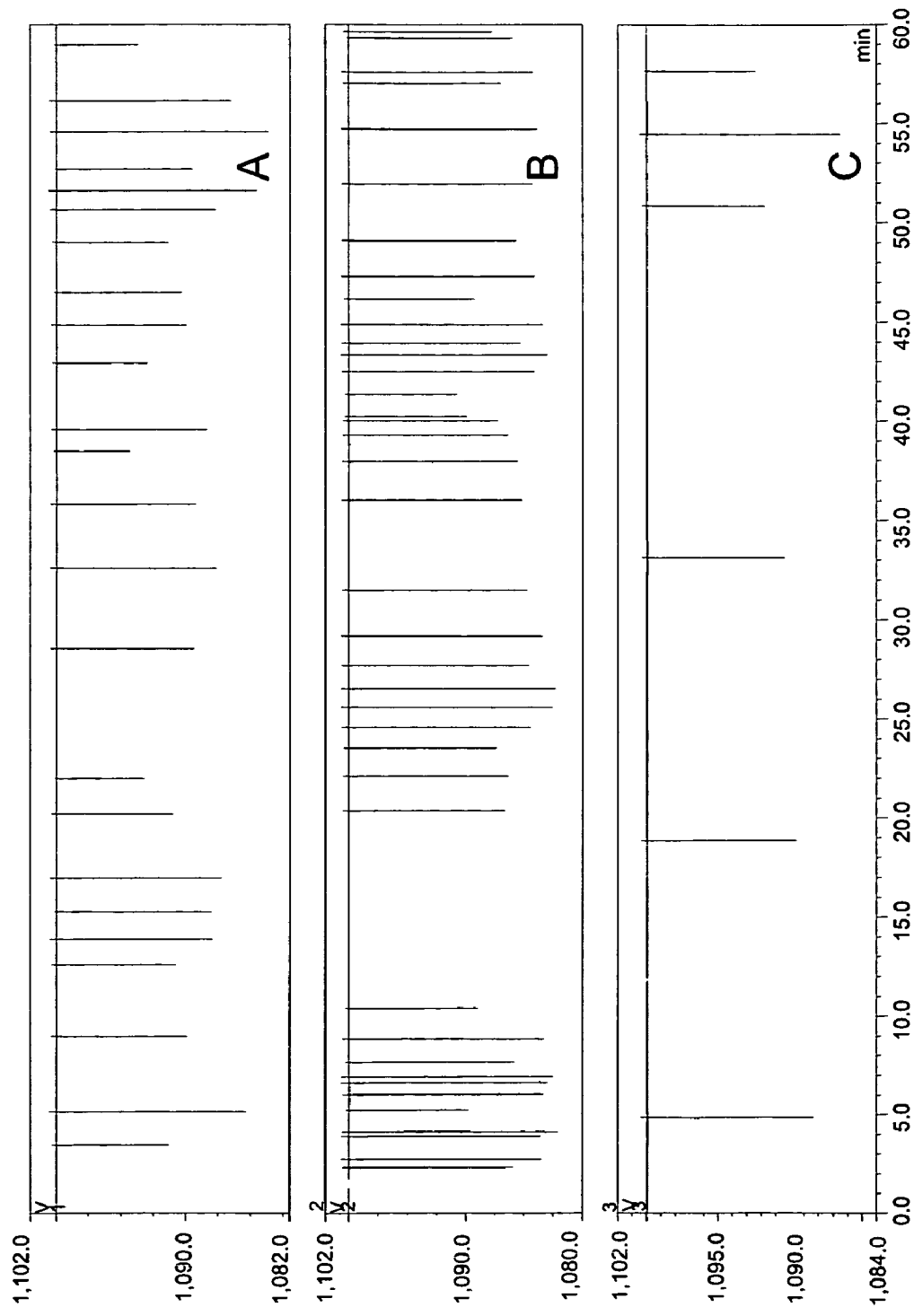

Example 8. The catalytic gas removal was tested for the ion exchange substrate of Example 7 (trace A, B & C of FIG. 14) and showed excellent gas removal for the combination metal catalyst as shown in Trace C.

Figure 15:
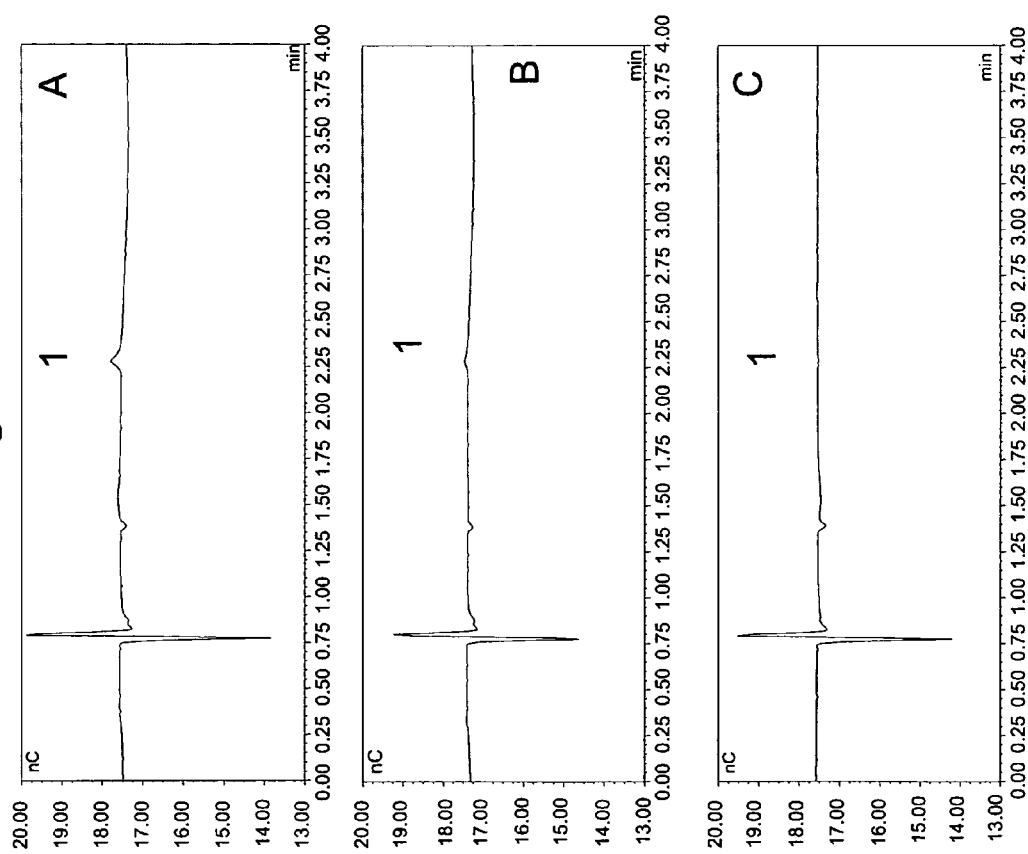
Figure 16:
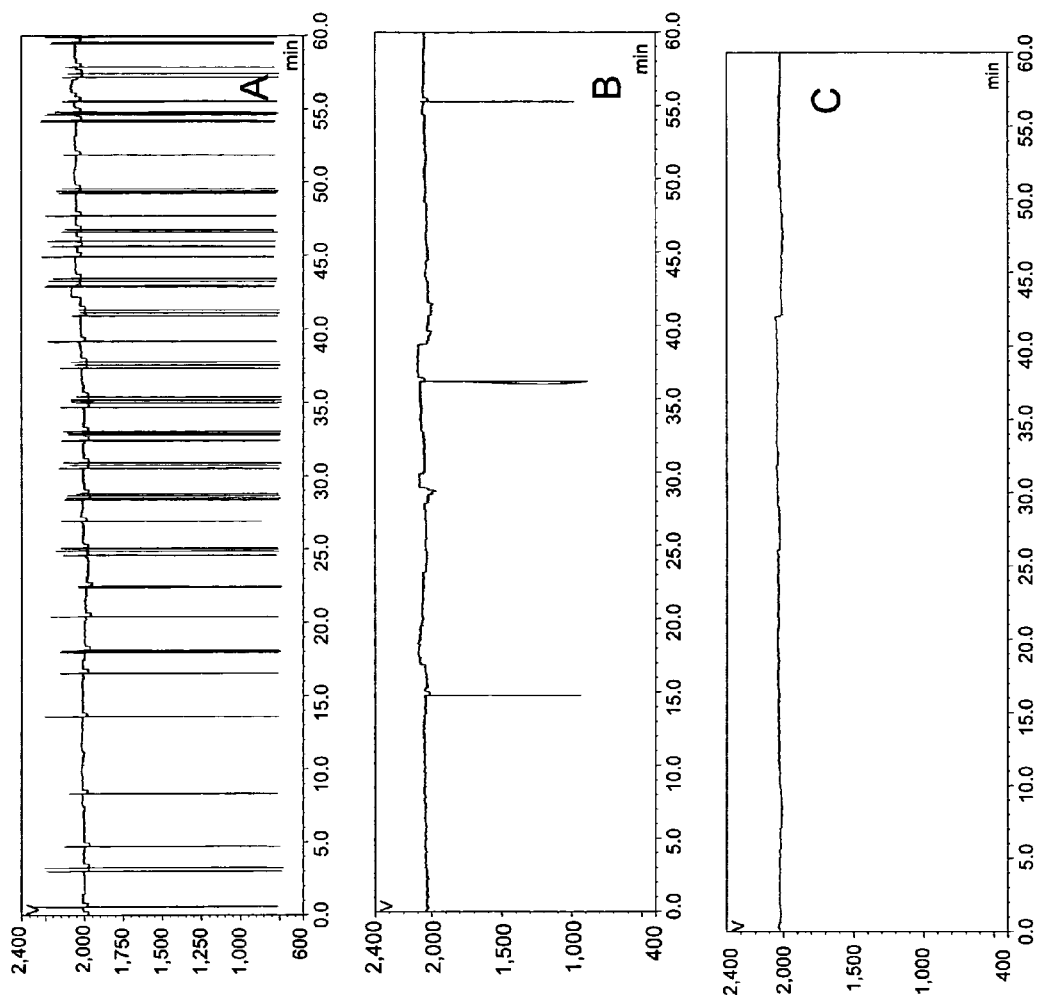

Example 9. A 50 um resin (Polystyrene 16% cross linked with divinylbenzene) fully sulfonated resin from Dionex Corporation was used as the substrate in this experiment. All other synthesis conditions were similar to Example 3 and the test setup was similar to Example 4. Referring to FIG. 15, the peroxide removal results showed the palladium (B) to outperform the platinum (A) and the combination (C) outperformed both. Complete removal was possible by the combination as apparent from a peak close to S/N ratios. Table 3 summarizes the results below. Also the catalytic gas removal efficiency was tested and showed platinum (A) to outperform palladium (B) and the combination coatings (C) with the two metals showed no bubbles and outperformed the single metal coatings (FIG. 16).

TABLE 3

A 50 um resin (Polystyrene 16% cross linked with divinylbenzene) fully sulfonated resin

| Catalyst Coating | Peak Area | Removal Efficiency % |
|---|---|---|
| None | 3.69 | |
| Palladium | 0.0045 | 99.88 |
| Platinum | 0.0163 | 99.56 |
| Palladium + Platinum | 0.0002 | 99.99 |

What is claimed is:

1. A chromatography apparatus comprising:
   (a) a chromatography column defining a column lumen,
   (b) flow-through chromatographic separation medium disposed in the column lumen, said separation medium defining liquid flow-through passages,
   (c) a detector,
   (d) a conduit for an aqueous liquid eluent stream providing fluid communication between said detector and said chromatographic separation medium,
   (e) a catalytic gas elimination chamber in fluid communication with said conduit and including a catalyst for combining hydrogen and oxygen gases, or for catalytically decomposing hydrogen peroxide, or both, in said eluent stream to form water and reduce the gas content in said eluent stream, and
   (f) a delay conduit disposed between said detector and said catalytic gas elimination chamber, said delay conduit having a total flow-through volume of at least 0.5 times the total volume of said separation medium flow-through passages.

2. The apparatus of claim 1 further comprising
   (g) an electrolytic eluent generator comprising flow-through suppressor ion exchange medium separated from an eluent generator chamber by a charged generator barrier, said suppressor ion exchange medium being in fluid communication with said delay conduit, and said eluent generator chamber being in fluid communication with a chromatography column.

3. The apparatus of claim 1 in which said catalytic gas elimination chamber comprises said delay conduit.

4. The apparatus of claim 1 further comprising:
   (f) a recycle line for directing effluent from said detector to said chromatographic separation medium.

5. The apparatus of claim 1 in which said delay conduit comprises a delay housing and said catalytic gas elimination chamber effluent flows through said housing in a tortuous path.

6. The apparatus of claim 1 in which said delay conduit comprises a flow-through coil.

7. The apparatus of claim 1 in which said delay conduit comprises a delay housing and a plurality of tubes, each tube being in parallel fluid communication with said detector.

8. The apparatus of claim 1 in which said delay conduit include a delay housing having a cross-sectional area transverse to fluid flow at least three times the cross-sectional area of said recycle conduit.

9. A chromatography apparatus comprising:
   (a) chromatographic separation medium,
   (b) a detector,
   (c) a membrane suppressor comprising a chromatography effluent flow channel, first and second detector effluent flow channels, and first and second ion exchange membranes separating said chromatography effluent flow channel from said first and second detector effluent flow channels, respectively, (d) a first conduit providing fluid communication between said separator medium and said chromatography effluent flow channel, (e) a second conduit providing fluid communication between said membrane suppressor chromatography effluent flow channel and said detector, (f) a third conduit providing fluid communication between said detector and said first detector effluent flow channel, (g) a fourth conduit providing fluid communication between said first and second detector effluent flow channels, (h) a fifth conduit providing fluid communication between said second detector effluent flow channel and said separation medium, and (i) a catalytic gas elimination device in fluid communication with at least one of said first, second or third conduits and including a catalyst for combining hydrogen and oxygen gases in at least one of said conduits.

10. A chromatography apparatus comprising:

(a) chromatographic separation medium, (b) a detector, (c) a conduit for an aqueous liquid eluent stream providing fluid communication between said detector and said chromatographic separation medium, (d) a catalytic gas elimination chamber in fluid communication with said conduit and including a catalyst for combining hydrogen and oxygen gases, or for catalytically decomposing hydrogen peroxide, or both, in said eluent stream to form water and reduce the gas content in said eluent stream, and (e) a bubble detector downstream of said catalytic gas elimination chamber and in fluid communication therewith.

11. A chromatography apparatus comprising:

(a) chromatographic separation medium, (b) a detector, (c) a conduit for an aqueous liquid eluent stream providing fluid communication between said detector and said chromatographic separation medium, (d) a catalytic gas elimination chamber in fluid communication with said conduit and including a catalyst for combining hydrogen and oxygen gases, or for catalytically decomposing hydrogen peroxide, or both, in said eluent stream to form water and reduce the gas content in said eluent stream, and (e) an energy generator disposed between and in fluid communication with said detector and said catalytic gas elimination chamber.

12. The apparatus of claim 11 in which said energy generator generates UV light.

13. The apparatus of claim 11 in which said energy generator generates heat.

* * * * *